(12) United States Patent
Montminy

(10) Patent No.: US 7,485,434 B2
(45) Date of Patent: Feb. 3, 2009

(54) METHOD FOR SCREENING COMPOUNDS FOR THOSE THAT MODULATE TRANSDUCERS OF REGULATED CREB ACTIVITY

(75) Inventor: Marc R. Montminy, San Diego, CA (US)

(73) Assignee: The Salk Institute for Biological Studies, La Jolla, CA (US)

( * ) Notice: Subject to any disclaimer, the term of this patent is extended or adjusted under 35 U.S.C. 154(b) by 116 days.

(21) Appl. No.: 11/398,477

(22) Filed: Apr. 4, 2006

(65) Prior Publication Data

US 2006/0246418 A1 Nov. 2, 2006

Related U.S. Application Data

(60) Provisional application No. 60/668,407, filed on Apr. 4, 2005.

(51) Int. Cl.
*C12Q 1/50* (2006.01)
(52) U.S. Cl. .......................................... 435/17
(58) Field of Classification Search ........................ None
See application file for complete search history.

(56) References Cited

OTHER PUBLICATIONS

Ahn, et al. (1998) A dominant negative inhibitor of CREB reveals that it is a general mediator stimulus dependent transcription of c-fos. *Molec. Cell. Biol.* 18: 967-977.
Al-Uzri, et al. (2001). Posttransplant diabetes mellitus in pediatric renal transplant recipients: a report of the North American Pediatric Renal Transplant Cooperative Study (NAPRTCS). Transplantation 72: 1020-1024.
Ararnburu, et al. (1998). Selective inhibition of NFAT activation by a peptide spanning the calcineurin targeting site of NFAT. Mol Cell 1: 627-637.
Arias, et al. (1994). Activation of CAMP and mitogen responsive genes relies on a common nuclear factor. Nature 370: 226-228.
Asahara, et al. (2001). Chromatin Dependent Cooperativity Between Constitutive and Inducible Activation Domains in CREB. Molecular and Cellular Biology 21: 7892-7900.
Banenjee, et al. (2004) Regulation of fasted blood glucose by resistin. Science 303: 1195-8.
Bergeron, et al. (2001) Effect of 5-aminoimidazole-4-carboxamide-1 -beta-Dribofuranoside infusion on in vivo glucose and lipid metabolism in lean and obese Zucker rats. *Diabetes* 50: 1076-82.
Bittinger, et al. (2004) Activation of cAMP response element-mediated gene expression by regulated nuclear transport of TORC proteins. *Curr Biol* 14: 2156-61.
Bonni, et al. (1995a). Serine 133 phosphorylated CREB Induces Transcription via a Cooperative Mechanism That May confer Specificity to Neurotrophin Signals. Molecular and Cellular Neurosciences 6: 168-183.
Brunet, et al. (1999). Akt promotes cell survival by phosphorylating and inhibiting a Forkhead transcription factor. Cell 96: 857-868.
Carling, D. (2004). The AMP-activated protein kinase cascade—a unifying system for energy control. Trends Biochem Sci 29: 18-24.
Chen, et al. (2003). Chk1 kinase negatively regulates mitotic function of Cdc25A phosphatase through 14-3-3 binding. Mol Cell Biol 23:7488-7497.
Chow and Davis (2000). Integration of calcium and cyclic AMP signaling pathways by 14-3-3. Mol Cell Biol 20:702-712.
Chrivia et al. (1993). Phosphorylated CREB binds specifically to the nuclear protein CBP. Nature 365: 855-859.
Conkright et al. (2003a). TORCs: transducers of regulated CREB activity. Mol Cell 12: 413-423.
Conkright et al. (2003b). Genome Wide Analysis of CREB Target Genes Reveals A Core Promoter Requirement for CAMP Responsiveness. Mol Cell 11: 1101-1108.

(Continued)

*Primary Examiner*—Jon P Weber
*Assistant Examiner*—Bin Shen
(74) *Attorney, Agent, or Firm*—Foley & Lardner LLP; Stephen E. Reiter

(57) ABSTRACT

In accordance with the present invention, it has been discovered that glucose and incretin hormones promote pancreatic islet cell survival via the calcium and cAMP dependent induction, respectively, of the transcription factor CREB. Specifically, a signaling module has been identified which mediates cooperative effects of calcium and cAMP on islet cell gene expression by stimulating the dephosphorylation and nuclear entry of TORC2, a cytoplasmic CREB coactivator. The module comprises a cAMP regulated snf1-like kinase called SIK2 and the calcium regulated phosphatase calcineurin, both of which associate with TORC2 in the cytoplasm. TORC2 is repressed under basal conditions through a phosphorylation dependent interaction with 14-3-3 proteins. cAMP and calcium signals stimulate CREB target gene expression via complementary effects on TORC2 dephosphorylation; cAMP disrupts TORC2-associated activity of SIK2 or related family members, whereas calcium induces TORC2 dephosphorylation via calcineurin. These findings provide a novel mechanism by which CREB activates cellular gene expression, depending on nutrient and energy status, and facilitate development of assays to identify compounds which modulate the role of TORCs. In accordance with the present invention, it has been discovered that fasting and energy-sensing pathways regulate the gluconeogenic program in liver by modulating the nuclear entry of a transcriptional coactivator called Transducer of Regulated CREB Activity 2 (TORC2). Hepatic TORC2 over-expression induces fasting hyperglycemia, whereas knockdown of TORC2 leads to fasting hypoglycemia and silencing of the gluconeogenic program. Since a majority of individuals with Type II diabetes exhibit fasting hyperglycemia due to elevated hepatic gluconeogenesis, compounds that enhance TORC2 phosphorylation will find use as therapeutic agents in this setting.

4 Claims, 16 Drawing Sheets

OTHER PUBLICATIONS

Crabtree and Olson (2002). NFAT signaling: choreographing the social lives of cells. Cell 109 Suppl, S67-79.

Doi et al. (2002). Salt inducible kinase represses CAMP-dependent protein kinase-mediated activation of human cholesterol side chain cleavage cytochrome P450 promoter through the CREB basic leucine zipper domain. J Biol Chem 277: 15629-15637.

Dougherty and Morrison (2004). Unlocking the code of 14-3-3. J Cell Science 117:1875-1884.

Durocher et al., (2000). The molecular basis of FHA domain:phosphopeptide binding specificity and implications for phospho-dependent signaling mechanisms. Mol Cell 6: 1169-1 182.

Enlund et al. (2004). Altered Notch signaling resulting from expression of a WAMTPI-MAML2 gene fusion in mucoepidermoid carcinomas and benign Warthin's tumors. Exp Cell Res 292: 21-28.

Filler et al. (2000). Tacrolimus reversibly reduces insulin secretion in paediatric renal transplant recipients. Nephrol Dial Transplant 15: 867-871.

Gonzalez and Montminy (1989). Cyclic AMP stimulates somatostatin gene transcription by phosphyorylation of CREB at Serine 133. Cell 59: 675-680.

Goodman and Smolik. (2000). CBPIp300 in cell growth, transformation, and development. Genes Dev 14: 1553-1577.

Hall and Granner (1999) Insulin regulates expression of metabolic genes through divergent signaling pathways. *J Basic Clin Physiol Pharmacol* 10: 119-133.

Hanson and Reshef (1997) Regulation of phosphoenolpyruvate carboxykinase (GTP) gene expression. *Annu Rev Biochem* 66: 581-611.

Herzig et al. (2001) CREB Regulates Hepatic Gluconeogenesis via the Co-activator PGC-I. *Nature* 413: 179-183.

Hogan et al. (2003) Transcriptional regulation by calcium, calcineurin, and NFAT. Genes Dev 17: 2205-2232.

Horike et al. (2003).Adipose-specific expression, phosphorylation of $Ser^{794}$ in insulin receptor substrate-1, and activation in diabetic animals of salt-induced kinase-2. J. Biol. Chem. 278:18440-18447.

Hui et al. (2003). Glucagon-like peptide-I inhibits apoptosis of insulin-secreting cells via a cyclic 5'- adenosine monophosphate dependent protein kinase A- and a phosphatidylinositol 3-kinase-dependent pathway. Endocrinology 144: 1444-1455.

Iourgenko et al. (2003). Identification of a family of cAMP response element-binding protein coactivators by genome-scale functional analysis in mammalian cells. Proc Natl Acad Sci U S A 100: 12147-52.

Jhala et al. (2003). cAMP promotes pancreatic beta-cell survival via CREB-mediated induction of LRS2. Genes Dev 17: 1575-1580.

Kahn et al. (2005) AMP-activated protein kinase: Ancient energy gauge provides clues to modem understanding of metabolism. *Cell Metabolism* 1: 15-25.

Kasper et al. (2002). A transcription-factor-binding surface of coactivator p300 is required for haematopoiesis. Nature 41 9: 738-743.

Katoh et al., (2004). Salt-inducible kinase (SIK) isoforms: their involvement in steroidogenesis and adipogenesis. Mol Cell Endocrinol 217:109-12.

Katoh et al. (2004) Salt-inducible kinase-I represses cAMP response element-binding protein activity both in the nucleus and in the cytoplasm. *Eur J Biochem* 271: 4307-19.

Koo et al. (2004) PGC-1 promotes insulin resistance in liver through PPAR-alpha dependent induction of TRB-3. *Nat Med* 10(5): 530-534 and 755.

Koo et al. (2005) The CREB coactivator TORC2 is a key regulator of fasting glucose metabolism. Nature 437: 1109-1114.

Kornhauser et al. (2002). CREB transcriptional activity in neurons is regulated by multiple, calcium-specific phosphorylation events. Neuron 34: 221-233.

Kwok et al. (1994). Nuclear protein CBP is a coactivator for the transcription factor CREB. Nature 370: 223-226.

Lemaigre et al. (1993). The cAMP response element binding protein, CREB, is a potent inhibitor of diverse transcriptional activators. Nucleic Acids Res 21:2907-2911.

Lin et al. (2004) Defects in adaptive energy metabolism with CNS-linked hyperactivity in PGC-I alpha null mice. *Cell* 119: 121-35.

Link et al. (1999) Direct analysis of protein complexes using mass spectrometry. Nat Biotechnol 17:676-682.

Lizcano et al. (2004) LKB1 is a master kinase that activates 13 kinases of the AMPK subfamily, including MARWAT-]. Embo J 23:833-843.

Lochhead et al.(2000) 5-aminoimidazole-4-carboxamide riboside mimics the effects of insulin on the expression of the 2 key gluconeogenic genes PEPCK and Glucose-6phosphatase. *Diabetes* 49: 896-903.

MasCoss et al. (2002) Shotgun identification of protein modifications from protein complexes and lens tissue. Proc Natl Acad Sci U S A 99: 7900-7905.

Mayr and Montminy (2001) Tanscriptional Regulation by the Phosphorylation Dependent Factor CREB. Nature Reviews-Molecular Cell Biology 2: 599-609.

Newgard and McGarry (1995) Metabolic coupling factors in pancreatic beta-cell signal transduction. Annu Rev Biochem 64: 689-719.

Newman and Keating (2003). Comprehensive identification of human bZIP interactions with coiled-coil arrays. Science 300: 2097-2101.

Okamoto et al. (2004) Salt-inducible kinase in steroidogenesis and adipogenesis. Trends Endocrinol Metab 15: 21-26.

Okamura et al. (2000) Concerted dephosphorylation of the transcription factor NFATI induces a conformational switch that regulates transcriptional activity. Mol Cell 6:539-550.

Parker et al. (1998) Analysis of an Activator:Coactivator Complex Reveals an Essential Role for Secondary Structure in Transcriptional Activation. Molecular Cell 2:353-359.

Radhakrishnan et al. (1997). Solution structure of the KIX domain of CBP bound to the transactivation domain of CREB: a model for activator-coactivator interactions. Cell 91: 741-752.

Radziuk et al. (2003) Metformin and its liver targets in the treatment of the type 2 diabetes. *Curr Drug Targets Immune Endocr Metabol Disord* 3: 151-69.

Sakamoto et al. (2004) Activity of LKB 1 and AMIPK-related kinases in skeletal muscle: effects of contraction, phenformin, and AICAR. *Am J Physiol Endocrinol Metab* 287: E310-317.

Saltiel and Kahn (2001) Insulin signaling and the regulation of glucose and lipid metabolism. Nature 414: 799-806.

Sasaki et al. (1984) Multihormonal regulation of phosphoenolpyruvate carboxykinase gene transcription. *J Biol Chem* 259:15242-15251.

Schwaninger et al. (1995). Involvement of the Ca(2+)-dependent phosphatase calcineurin in gene transcription that is stimulated by cAMP through cAMP response elements. J Biol Chem 270: 8860-8866.

Screaton et al. (2004) The CREB coactivator TORC2 functions as a calcium- and cAMP-sensitive coincidence detector. *Cell* 119: 61-74.

Shaw et al. (2004). The tumor supressor LKBI kinase directly activates AMP activated kinase and regulates apoptosis in response to energy stress. Proc. Natl Acad Sci U S A 101:3329-3335.

Shaywitz and Greenberg (1999). CREB: A Stimulus-Induced Transcription Factor Activated by A Diverse Array of Extracellular Signals. Annu Rev Biochem 68: 821-861.

Sheng et al. (1991). CREB: A Ca-Regulated Transcription Factor Phosphorylated by Calmodulin-Dependent Kinases. Science 252: 1427-1430.

Tabb et al. (2002). DTASelect and Contrast: tools for assembling and comparing protein identifications from shotgun proteomics. Journal of Proteome Research 1:21-26.

Tonon, et al. (2003). t(11;19)(q21;p13) translocation in mucoepidermoid carcinoma creates a novel fusion product that disrupts a Notch signaling pathway. Nat Genet 33:208-213.

Yoon et al. (2001) Control of hepatic gluconeogenesis through the transcriptional coactivator PGC-1. *Nature* 413, 131-138.

Woods et al. (2003). LKBI is the upstream kinase in the AMP-activated protein kinase cascade. Curr Biol 13: 2004-2008.

Yamauchi et al. (2002) Adipoenctin stimulates glucose utilization and fatty-acid oxidation by activating AMP-activated protein kinase. *Nat Med* 8: 1288-95.

FIGURE 15

Table $^{32}$P-incorporation into GST-fusion peptides by SIK kinase domain

| Protein (Target residue) | Accession No. | Peptide[1] | Class[2] |
|---|---|---|---|
| Syntide2 (Ser7) | Synthetic | PLARTLSVAGLPGKK | I |
| Human p300 (Ser89) | UO 1877 | LLRSGSSPNL | |
| Human HDAC5 (Ser259) | AF132608 | LRKTASEPNL | |
| Human tRep (Ser132) | AF297872 | LCRSNSIDGS | |
| Mouse cdc2SB (Ser321) | NM_023117 | LFRSPSMPCSVR | II |
| Rat IRS1 (SEr789) | NM_012969 | LRLSSSSGRL | |
| Mouse PGC1a (Ser284) | BCO66868 | IERTLSVELS | |
| GSK-synthetic (Ser7) | Synthetic | PLSRTLSVAAK | |
| SAMS4[3] (Ser7) | Synthetic | HLMRSASGMHLVKRR | |
| Human HDAC5 (Ser498) | AF132608 | LSRTQSSPLP | III |
| Human HDAC5 (Ser661) | AF132608 | LGRTQSSPAA | |
| Mouse jdp2 (Ser 145) | NM_030887 | IVRTDSVRTP | |
| Human p300 (S89T[4]) | UO1877 | LLRSGTSPNL | |
| SAMS3[3] (Ser7) | Synthetic | HMMRSASGMHLVKRR | |
| Human p300 (S89A[4]) | U01877 | LLRSGASPNL | IV |
| Human CBP (Ser78) | AAC51331 | LLRGGSGSSI | |
| Human SMRT (Thr35) | AAD22973 | IARTHTDVGL | |
| Rat SIK1(Thr49) | A13020480 | ARHRVTKTQVAIK | |
| Rat SIK1 (Thr268) | AB02040S | PAKRITIAQIRQH | |
| Rat SIK1 (Thr322) | AB02040S | IDRQRTVESLQN | |
| Rat ZPK (Ser432) | BAA08621 | FEKIKSEGTCLHR | |
| Rat ZPK (Ser510) | BAA08621 | LKSHPSRGLLH | |
| Rat ZPK (Ser518) | BAA08621 | LLHGDTMEKLIKKR | |
| SAMS[3] (Ser7) | Synthetic | HMRSAMSGLHLVKRR | |
| SAMS2[3] (Ser7) | Synthetic | HMRSAMSGMHLVKRR | |
| SAMS5[3] (Ser7) | Synthetic | HLMRSATGMHLVKRR | |
| SIK consensus | | L-x-R-S/T-x-S-x-x-x-L | |

1) bold letters indicate residues conserved in the AMPK consensus [H-(B-X or X-B)-X-X-S-X-X-X-H].
2) relative $^{32}$P-incorporation compared with Syntide2; I, >80%; II, 80-20%; III, <20%; IV, undetectable.
3) synthetic substrates of AMPK, SAMS peptide and modified peptides.
4) amino acid substitution.

METHOD FOR SCREENING COMPOUNDS FOR THOSE THAT MODULATE TRANSDUCERS OF REGULATED CREB ACTIVITY

RELATED APPLICATION

This application claims priority from U.S. Patent Application No. 60/668,407 filed Apr. 4, 2005, the entire contents of which is hereby incorporated by reference herein.

FIELD OF THE INVENTION

The present invention relates to methods for screening compounds to determine if such compounds are capable of enhancing islet cell activity and/or survival, capable of promoting CREB-mediated gene expression in islet cells, capable of effecting transport of Transducers of Regulated CREB (TORCs) from the cytoplasm into the nucleus of an islet cell, capable of effecting interactions between TORCs and member(s) of the 14-3-3 family of proteins, and the like. In additional aspects, the present invention relates to methods for enhancing islet cell activity and/or survival.

BACKGROUND OF THE INVENTION

Under feeding conditions, elevations in blood glucose and circulating incretin hormones such as glucagon like peptide-1 (GLP-1) stimulate islet survival in part via the activation of the transcription factor CREB (Jhala et al., 2003). Elevations in glucose stimulate insulin secretion and islet cell gene expression via closure of KATP channels and subsequent influx of calcium through activated L-type calcium channels (Newgard and McGarry, 1995). In contrast, GLP-1 has been found to promote islet cell survival and proliferation by activation of the cAMP pathway (Hui et al., 2003). Transgenic mice expressing a dominant negative CREB polypeptide in islets develop diabetes with apoptosis of insulin producing beta cells due in part to reduced expression of IRS2, a direct target of CREB activity (Jhala et al., 2003).

cAMP promotes the expression of cellular genes by triggering the PKA mediated phosphorylation of CREB at Ser133 (Gonzalez and Montminy, 1989). Phosphorylation of CREB at Ser133 in turn stimulates target gene expression by enhancing recruitment of the histone acetylase coactivator paralogs CBP and P300 (Arias et al., 1994; Chrivia et al., 1993; Kwok et al., 1994). The structure of the CREB:CBP complex, using relevant interaction domains, called KID and KIX, respectively, reveals that phospho (Ser133) forms direct contacts with residues in KIX that account for half of the free energy of complex formation (Parker et al., 1998; Radhakrishnan et al., 1997). Binding of KID to KIX also promotes a random coil to helix transition in KID that favors formation of hydrophobic contacts with residues lining a shallow groove in KIX.

In addition to cAMP, CREB is Ser 33 phosphorylated in response to a number of stimuli, including growth factors, shear stress, and UV light (Mayr and Montminy, 2001). A number of these stimuli, however, are incapable of promoting target gene activation via CREB per se due in part to secondary phosphorylation of CREB at inhibitory sites. Neuronal depolarization triggers phosphorylation of CREB not only at Ser133 but also at Ser142 and Ser143 (Kornhauser et al., 2002), for example, and these modifications destabilize the CREB:CBP complex by electrostatic repulsion (Kornhauser et al., 2002; Parker et al., 1998).

The ability of calcium signals to promote CREB dependent transcription while apparently blocking CBP recruitment, at least via the KID domain, is indicative of the potential presence of other coactivators that either mitigate these effects or function independently of CBP/P300. The involvement of a distinct CREB coactivator in promoting calcium dependent gene expression is further indicated by studies in which addition of calcineurin antagonists are observed to block calcium-stimulated CREB activity without affecting levels of CREB Ser133 phosphorylation (Schwaninger et al., 1995). The identification of such putative coactivator(s), however, remains elusive.

Although the KID domain in CREB is thought to mediate target gene activation in response to most extracellular stimuli, other regions, most notably the bZIP DNA binding/dimerization domain, have also been implicated in this process. In previous studies using GAL4-CREB fusion proteins to define domain requirements for transcriptional activation, for example, both KID and bZIP domains were found to contribute importantly to cAMP and KCl responsiveness (Bonni et al., 1995a; Sheng et al., 1991). These results are also indicative of the involvement of additional cofactors that promote cAMP and calcium dependent transcription through an interaction with the CREB bZIP domain. Consistent with the ability of this region to recruit components of the transcriptional apparatus, the CREB bZIP domain has been found to act as a potent repressor of numerous transcription factors when over-expressed in various cells (Lemaigre et al., 1993).

Accordingly, there is a need in the art for methods to identify compounds that modulate the above-described interactions. Such compounds will find use in a variety of applications, such as, for example, enhancing islet cell activity and/or survival, promoting CREB-mediated gene expression in islet cells, effecting transport of Transducers of Regulated CREB (TORCs) from the cytoplasm into the nucleus of islet cells, effecting interactions between TORCs and member(s) of the 14-3-3 family of proteins, and the like.

SUMMARY OF THE INVENTION

In accordance with the present invention, it has been discovered that glucose and incretin hormones promote pancreatic islet cell survival via the calcium and cAMP dependent induction, respectively, of the transcription factor CREB. Specifically, a signaling module has been identified which mediates cooperative effects of calcium and cAMP on islet cell gene expression by stimulating the dephosphorylation and nuclear entry of TORC2, a cytoplasmic CREB coactivator. The module comprises a cAMP regulated sucrose-non-fermenting-1 (snf1)-like protein kinase called SIK2 (and related family members) and the calcium regulated phosphatase calcineurin, both of which associate with TORC2 in the cytoplasm. TORC2 is repressed under basal conditions through a phosphorylation dependent interaction with 14-3-3 proteins. cAMP and calcium signals stimulate CREB target gene expression via complementary effects on TORC2 dephosphorylation; cAMP disrupts the TORC2-associated activity of SIK2 and related family members, whereas calcium induces TORC2 dephosphorylation via calcineurin. The results described herein establish that glucose and incretin hormones exert synergistic effects on CREB activity and islet cell survival by targeting a signaling module that contains TORC2-associated kinase and phosphatase activities, respectively.

In recent high-throughput expression screens to identify novel modulators of CREB activity, a family of CREB coactivators, referred to as Transducers of Regulated CREB activity (TORCs) have been characterized (see, for example, Conkright et al., 2003a; and Iourgenko et al., 2003). The three exemplary TORC family members identified thus far share a highly conserved N-terminal coiled-coil domain that mediates a direct association with the bZIP domain of CREB. The present disclosure establishes that TORC2 is a cytoplasmic co-factor that translocates to the nucleus in response to cAMP and calcium signals where it modulates CREB target gene expression. TORC2 shuttling activity is regulated by associated protein kinase (e.g., SIK2 or related family members) and phosphatase (e.g., calcineurin) activities that modulate levels of TORC phosphorylation. These findings provide a novel mechanism by which CREB activates cellular gene expression, depending on nutrient and energy status, and facilitate development of assays to identify compounds which modulate the role of TORCs.

Mammals achieve energy balance by modulating hepatic glucose output depending on nutritional status (Saltiel and Kahn, 2001). Elevations in glucagon during fasting trigger the gluconeogenic program, for example, via the cAMP responsive factor CREB (Herzig et al., 2001). By contrast, exercise and other stressors that deplete cellular ATP levels inhibit gluconeogenesis via the AMP kinase pathway, although the underlying mechanism has remained elusive (Kahn et al., 2005). In accordance with the present invention, it has been discovered that fasting and energy-sensing pathways regulate the gluconeogenic program in liver by modulating the nuclear entry of a transcriptional coactivator called Transducer of Regulated CREB Activity 2 (TORC2) (see, for example, Conkright et al., 2003a; Iourgenko et al., 2003; Screaton et al., 2004; and Bittinger et al., 2004). Thus, under feeding conditions, TORC2 is sequestered in the cytoplasm via phosphorylation at Ser171 (see Screaton et al., 2004).

Glucagon administration promotes rapid Ser171 dephosphorylation, nuclear translocation, and recruitment of TORC2 to gluconeogenic promoters in liver. Hepatic TORC2 over-expression induces fasting hyperglycemia, whereas knockdown of TORC2 leads to fasting hypoglycemia and silencing of the gluconeogenic program. Following prolonged exposure to glucagon, TORC2 activity is attenuated by a negative feedback loop involving the CREB mediated induction of SIK1, a Ser/Thr kinase that phosphorylates TORC2 at Ser171 (Screaton et al., 2004; and Katoh et al., 2004). Knockdown of SIK1 enhances TORC2 activity on gluconeogenic genes, whereas SIK1 over-expression silences the gluconeogenic program and promotes fasting hypoglycemia in mice. Similarly, induction of the AMPK (AMP-activated protein kinase) pathway with an AMP analog inhibits TORC2 activity on gluconeogenic genes; these effects are rescued by expression of phosphorylation-defective Ser171Ala TORC2. Since a majority of individuals with Type II diabetes exhibit fasting hyperglycemia due to elevated hepatic gluconeogenesis, compounds that enhance TORC2 phosphorylation will find use as therapeutic agents in this setting.

BRIEF DESCRIPTION OF THE FIGURES

FIG. 1B presents quantitative PCR (Q-PCR) analysis of the CREB target gene NR4A2 in MIN6 insulinoma cells exposed to glucose (20 mM) and/or exendin-4 (10 nM). The effect of the calcium channel antagonist, nifedipine, and CsA are shown.

FIG. 1C is a Western blot assay of phospho (Ser133) CREB levels in HIT cells following treatment with KCl (45 mM), forskolin (10 μM), or both together for 30 minutes. The effect of CsA treatment on levels of phospho (Ser133) CREB is indicated.

FIG. 1D illustrates the effect of calcium and cAMP agonists on CREB:CBP complex formation. A mammalian two-hybrid assay was carried out employing HIT cells transfected with GAL4-KID and KIX-VP 16 expression plasmids. The luciferase activity from cells co-transfected with GAL4 luciferase reporter is shown. Cells were treated with forskolin and KCl (6 hours), alone and in combination, as indicated.

FIG. 1E illustrates the effect of KCl and forskolin on the activity of full-length GAL4-CREB and truncated GAL4-CREB AbZIP polypeptides lacking the bZIP domain (amino acid residues 284-341) in transfected HIT cells. Treatment with CsA is shown.

FIG. 2B illustrates the effect of TORC2 knockdown on induction of EVX-1 reporter in response to cAMP. The left panel illustrates a transient assay of HEK293T cells co-transfected with non-specific or TORC2 RNAi plasmid plus EVX-1 reporter. The right panel illustrates the rescue of activity with TORC3 expression plasmid shown. The inset presents a Western blot assay of endogenous TORC2 protein levels in TORC2 RNAi or non-specific RNAi transfected cells.

FIG. 2C summarizes the results of transient transfection assays of HIT cells expressing wild-type and mutant GAL4-CREB polypeptides that are defective in either CBP (M1: Ser133Ala) or TORC (M2: Arg314Ala) binding. Comparable expression of wild-type and mutant GAL4-CREB polypeptides was confirmed by Western blot assay (not shown). The effect of forskolin (F) and KCl (K), either alone or in combination, on co-transfected GAL4 luciferase reporter is shown. Treatment with CsA is indicated.

FIG. 2D presents the results of chromatin immunoprecipitation assay of HEK293T cells using CREB, CBP, and TORC2 (T2) specific antisera. PCR amplification of the cAMP responsive NR4A2 promoter (5') and 3' flanking region fragments from CREB, CBP, and TORC2 immunoprecipitates is shown. The effect of forskolin treatment (30 min) is indicated. Linearity of the PCR assay with decreasing DNA input levels is also indicated.

FIG. 3A presents fluorescence microscopic analysis of Flag-tagged TORC2 in human ATYBI fibroblasts treated with forskolin (10 μM) or control vehicle for 30 minutes as indicated.

FIG. 3B illustrates the effect of exportin inhibitor leptomycin B (LMB) on nuclear targeting of TORC2 in transfected ATYB1 fibroblasts. DAPI staining is shown alongside to indicate nuclei.

FIG. 3C, top panel, illustrates the effect of Tyr282 to Phe mutagenesis in NES1 on TORC3 localization in control and forskolin treated ATYB1 cells. Wild-type TORC3 staining in control cells is also shown. FIG. 3C, bottom panel, presents amino acid sequence alignments for NES1 and NES2 motifs in TORC1, TORC2, and TORC3, relative to consensus NES motif shown below (SEQ ID NOS: 10-16, respectively, in order of appearance. Residue Tyr282 in TORC3 is highlighted.

FIG. 3D, top panel, presents a comparison of basal TORC2 (T2) and TORC3 (T3) activities in HEK293T cells cotransfected with EVX-1 reporter. Comparable expression of TORC2 and TORC3 proteins was confirmed by Western blot analysis (not shown). The effect of N-terminal src myristylation tag on TORC2 and TORC3 activities is shown. FIG. 3D, bottom panel, demonstrates the effect of adding the Tyr282Phe mutation on basal TORC3 activity, relative to empty vector control in HIT cells co-transfected with EVX-1 reporter.

FIG. 4A, right panel, illustrates the effect of calf intestinal alkaline phosphatase (CIP) treatment on the electrophoretic mobility of cytoplasmic TORC2.

FIG. 4B illustrates the effect of co-stimulation with forskolin and KCl (F+K: 30 minutes) on endogenous TORC2 phosphorylation in HIT cells. Treatment with CsA is indicated.

FIG. 4C, top panel presents an SDS-PAGE analysis of $^{32}$P-labeled Flag-TORC2 immunoprecipitates from transfected HIT cells incubated with inorganic $^{32}$P. Control cells transfected with empty vector (vec) are also indicated. Treatment with forskolin (F), KCl (K), or forskolin plus KCl are shown. The effect of CsA is indicated. FIG. 4C, middle panel, presents a Western blot assay of immunoprecipitated $^{32}$P labeled TORC2 protein from top panel. FIG. 4C, bottom panel, illustrates the relative levels of TORC2 phosphorylation for each treatment, normalized to the immunoprecipitated TORC2 protein levels shown.

FIG. 5A, bottom left panel, is a Western blot assay of 14-3-3 proteins recovered from TORC or control 1 gG immunoprecipitates, illustrating the effect of forskolin treatment on endogenous TORC: 14-3-3 complexes in PC12 and HEK293T cells. Input levels of 14-3-3 and TORC proteins are shown. Comparable recovery of endogenous TORC proteins from TORC immunoprecipitates is indicated. FIG. 5A, bottom right panel, illustrates the kinetics of TORC2 dissociation from endogenous 14-3-3 proteins in response to forskolin treatment of HEK293T cells. The levels of Flag-tagged TORC 2 (FLAG-T2) recovered from flag immunoprecipitates at each time point is shown below.

FIG. 5B summarizes the results of co-immunoprecipitation assays using truncated TORC2 polypeptides to define the 14-3-3 interaction site. The deletion endpoints in TORC2 are shown.

FIG. 5C illustrates the effect of 14-3-3 beta over-expression on EVX-1 reporter activity in HEK293T cells co-transfected with wild-type TORC2, 14-3-3 interaction defective (A56-547) TORC2, or empty vector.

FIG. 5D demonstrates that TORC2 binds to calcineurin. A pull-down assay of GST-calcineurin A (amino acid residues i-347) with $^{35}$S-labeled wildtype and mutant TORC2 polypeptides containing internal deletions are indicated.

FIG. 6B summarizes immunoprecipitation assays of HEK293T cells co-transfected with expression vectors for SIK2 and Flag-tagged TORC2. Western blot assays of SIK2 recovered from Flag immunoprecipitates using anti-SIK2 antiserum are shown.

FIG. 6C identifies phosphopeptides recovered from Flag-tagged TORC2 immunoprecipitates identified by MSMS analysis (SEQ ID NOS: 17-27, respectively, in order of appearance). Amino acid endpoints and phosphorylated residues are indicated. Consensus SIK2 phosphorylation site shown: φ=hydrophobic; B=basic, X=any amino acid.

FIG. 6D demonstrates that SIK2 phosphorylates TORC2 at Ser171. An in vitro kinase assay of wild-type and Ser171Ala GST TORC2 polypeptides (amino acid residues 162-179) was conducted using purified SIK2 as indicated. The effect of SIK2 (or related family members) on phosphorylation of GST alone or GST-syntide 2 containing a consensus SIK2 phosphorylation site (PLARTLSVAGLPGKK; SEQ ID NO:1) is shown. Input levels of individual GST proteins (CBB) are shown below.

FIG. 7A presents a Western blot analysis of total and phospho (Ser587)-SIK2 levels in COS-7 cells transfected with wild-type and PKA phosphorylation defective Ser587Ala mutant SIK2 expression vector. The effect of forskolin treatment is shown.

FIG. 7B, left panel, presents a comparison of wild-type, PKA phosphorylation defective (Ser587Ala), and kinase-inactive (Lys49Met) SIK2 constructs on EVX-1 reporter activity in control and forskolin treated HEK293T cells. FIG. 7B, right panel, illustrates the effect of wild-type and Ser171 Ala mutant TORC2 polypeptides on EVX-1 reporter activity in control and forskolin stimulated HEK293T cells.

FIG. 7C, top panels, illustrate the effect of SIK2 (or related family members) on TORC2 subcellular localization. Immunofluorescence microscopy is presented for ATYB1 cells transfected with Flagtagged TORC2 plus wild-type or PKA phosphorylation defective SIK2 (Ser587Ala) as indicated. DAP1 staining is shown below each panel. FIG. 7C, bottom panels, illustrate the effect of Ser171 Ala mutagenesis on cellular localization of TORC2. Treatment with forskolin is indicated.

FIG. 13, bottom panel, illustrates the effect of LMB treatment on TORC1 localization in ATYBI cells transfected with flag-tagged TORC1 expression vector. TORC1 localization was followed using anti-flag antiserum. DAP1 staining is shown alongside.

FIG. 15 provides the characterization of optimal phosphorylation sites for SIK2. Potential SIK2 substrates identified in database search were tested by in vitro kinase assay with purified SIK2. The table shows the substrates tested and the relative stoichiometry of phosphorylation. The optimal motif for SIK2 mediated phosphorylation is shown. FIG. 15 discloses SEQ ID NOS: 1 and 28-53, respectively, in order of appearance.

FIG. 16A presents an immunohistochemical analysis of CREB and phospho (Ser133) CREB staining on liver sections from mice 10 minutes following intraperitoneal (IP) injection with insulin, glucagon, or vehicle (PBS). DAP1 staining is shown to highlight nuclei.

FIG. 16B presents a Western blot analysis of phospho (Ser133) CREB and CREB levels in liver extracts prepared from the same three treatment groups as described above.

FIG. 16C presents an immunohistochemical analysis of TORC2 localization in liver sections from mice 10 minutes following the same intraperitoneal (IP) injections as described above with respect to FIG. 16A. DAP1 staining is shown to highlight nuclei.

FIG. 16D presents a Western blot assay of HA-TORC2 immunoprecipitates prepared from whole liver extracts of treatment groups described above with anti-HA antiserum. Western blotting with phospho (Ser171) specific and non-discriminating TORC2 antiserum is shown. The top band in the glucagon treated sample corresponds to Ser171-phosphorylated (PTORC2).

FIG. 16E presents the results of a Chromatin Immunoprecipitation (ChIP) Assay of liver extracts from mice 10 minutes following IP glucagon or insulin administration. The recruitment of TORC2 to CREB target genes (PEPCK, G6Pase) in liver is demonstrated. FDPS, CREB target gene is induced only in the fed state (FDPS) in liver. Levels of TORC2 recruitment to each gene were determined by Q-PCR analysis.

FIG. 17A illustrates the effect of TORC2 on induction of gluconeogenic genes (PEPCK, PGC-1α, G6Pase) by FSK (10 µM, 2 hr) in cultured primary rat hepatocytes infected with TORC2 or control GFP adenovirus as indicated.

FIG. 17B demonstrates that TORC2 stimulates gluconeogenic genes via CREB. The effect of dominant negative A-CREB (AC) adenovirus on G6Pase mRNA levels is illustrated in cells co-infected with GFP or TORC2 adenovirus and treated with FSK as indicated.

FIG. 17C summarizes the effect of TORC on glucose output from primary rat hepatocytes in response to fasting and feeding signals. Cells were infected with TORC1, TORC2, or control GFP adenovirus and then treated with FSK plus dexamethasone (FSK/DEX) for four hours. The effect of insulin on glucose output is shown.

FIG. 17D summarizes the effect of TORC2 over-expression on fasting glucose metabolism. Blood glucose levels in control (GFP) and TORC2 adenovirus injected mice is shown, taken sequentially after 7 and 24 hours of fasting (n=3). Below the graph presented in FIG. 17D, a Western blot analysis of liver extracts from control and TORC2 adenovirus infected mice is presented, showing the relative levels of endogenous and adenovirus expressed HA-TORC2 (denoted by an arrow).

FIG. 17E summarizes the effect of acute TORC2 knockdown on fasting glucose levels in mice (n=3). Mice were infected with TORC2 RNAi or unspecific (US) RNAi adenovirus. The inset presents a Western blot assay of TORC2 levels in primary hepatocytes infected with unspecific on TORC2 RNAi adenovirus.

FIG. 17F presents a Q-PCR analysis of hepatic mRNAs from TORC2 deficient (TORC2 RNAi) and control (US) mice. The levels of gluconeogenic (PEPCK, PGC-1α, G6Pase, PC) and mitochondrial (Cox4, Cyt-C) gene expression are shown.

FIG. 18A illustrates the time course of PEPCK gene expression in primary rat hepatocytes following exposure to FSK. mRNA levels were determined by Q-PCR analysis.

FIG. 18B illustrates the effect of CHX on levels of phospho (Ser171) TORC2 in primary rat hepatocytes treated with glucagon over a variety of time points, shown in hours. Western blot assay indicates the levels of TORC2, phospho (Ser171) TORC2 and CREB.

FIG. 18C illustrates the effect of CHX pretreatment on induction of gluconeogenic genes (PEPCK, PGC-1α, G6Pase) by glucagon in primary rat hepatocytes. Relative mRNA levels are shown.

FIG. 18D summarizes the effect of fasting on mRNA levels for SIK1, SIK2, and SIK3 genes in liver by Q-PCR anlaysis (n=3).

FIG. 18E presents a Western blot analysis of SIK1 protein levels in whole liver extracts from mice under ad libitum, fasting, or refed conditions. CREB levels are shown for comparison.

FIG. 18F summarizes the effect of FSK treatment on SIK1 mRNA levels in primary rat hepatocytes. Cells were infected with control (GFP) or dominant negative A-CREB adenovirus as indicated.

FIG. 18G summarizes the effect of co-transfected PKA, dominant negative A-CREB, or control (empty) expression vector on SIK1 luciferase reporter activity in transiently transfected HepG2 hepatocytes.

FIG. 18H, top, provides a schematic of a SIK1 promoter, showing the presence of two CRE sites at positions indicated relative to the transcriptional start site. FIG. 18H, bottom, presents the results of a Chromatin Immunoprecipitation (ChIP) assay of CREB immunoprecipitates prepared from SV40-transformed mouse hepatocytes, showing recovery of SIK1 promoter or negative control ACT B promoter, which lacks consensus CREB binding site. Genomic DNA input (In) levels (1%) are shown.

FIG. 19A, bottom, presents a Western blot assay with nondiscriminating TORC2 antiserum, showing the effect of SIK1 RNAi adenovirus on TORC2 dephosphorylation (compare P-TORC2 and TORC2 bands) following exposure of primary rat hepatocytes to glucagon (Gluc). The arrow identifies phosphorylated TORC2.

FIG. 19B summarizes the effect of SIK1 RNAi on gluconeogenic gene expression in primary rat hepatocytes, presenting Q-PCR analysis showing the relative induction of PEPCK, PGC-1α, and G6Pase mRNAs by glucagon in cells infected with control (US) or SIK1 RNAi expressing adenoviruses.

FIG. 19C summarizes the effect of SIK1 and SIK2 relative to control (GFP) adenovirus injection on fasting glucose levels in mice (n=4).

FIG. 19D presents a Q-PCR analysis of gluconeogenic gene expression (PEPCK, G6Pase, PGC-1α) in livers of fasted mice infected with control (GFP), SIK1, or SIK2 Adenovirus.

FIGS. 19E and 19F demonstrate the role of Ser171 in TORC2 for SIK1 inhibition of gluconeogenic genes. Specifically, the effect of SIK1 on the induction of gluconeogenic PGC-1α (see FIG. 19E) and PEPCK (see FIG. 19F) genes by wild-type and Ser171Ala TORC2 is illustrated in primary rat hepatocytes.

FIG. 20A illustrates the relative phosphorylation of wild-type or Ser171 Ala mutant recombinant GST-TORC2 (161-181) compared to GST only or optimal AMPK peptide substrate (SAMS) by activated AMPK in vitro. Addition of AMP to reactions is shown. The relative incorporation of $\gamma^{32}P$-ATP by each substrate is indicated.

FIG. 20B demonstrates the effect of the AMP analog AICAR (1 mM) on phosphorylation of endogenous TORC2 in primary rat hepatocytes. Cells were exposed to AICAR and FSK for 30 minutes. Lower mobility bands (arrow) indicate phosphorylated TORC2 polypeptides.

FIG. 20C illustrate the effect of AICAR and SIK1 on cellular localization of wild-type or Ser171 Ala TORC2 in primary rat hepatocytes. Cells were infected with adenoviruses for HA-tagged wild-type or mutant TORC2 and SIK1 as indicated. Infected cells were exposed to FSK and AICAR for 30 minutes. TORC2 localization was examined with anti-HA antiserum. Cells were counterstained with DAP1 to visualize nuclei.

FIG. 20D summarizes the effect of AlCAR on expression of gluconeogenic genes (PEPCK, PGC-1α) in primary rat hepatocytes. Cells infected with mutant Ser171Ala TORC2 (171) adenovirus indicated. Treatment with AICAR and FSK is shown.

FIG. 20E illustrates an auto-regulatory loop which controls gluconeogenic gene expression in liver. Activation of the cAMP pathway by glucagon triggers expression of the gluconeogenic program via acute Ser171 dephosphorylation and activation of TORC2. At late times after glucagon stimulation TORC2 activity is attenuated via CREB-mediated induction of SIK1, which in turn rephosphorylates TORC2 at Ser171. In response to ATP depletion, TORC2 activity is also inhibited by AMPK (AMP-activated protein kinase) mediated phosphorylation at Ser171.

DETAILED DESCRIPTION OF THE INVENTION

Figure 1:
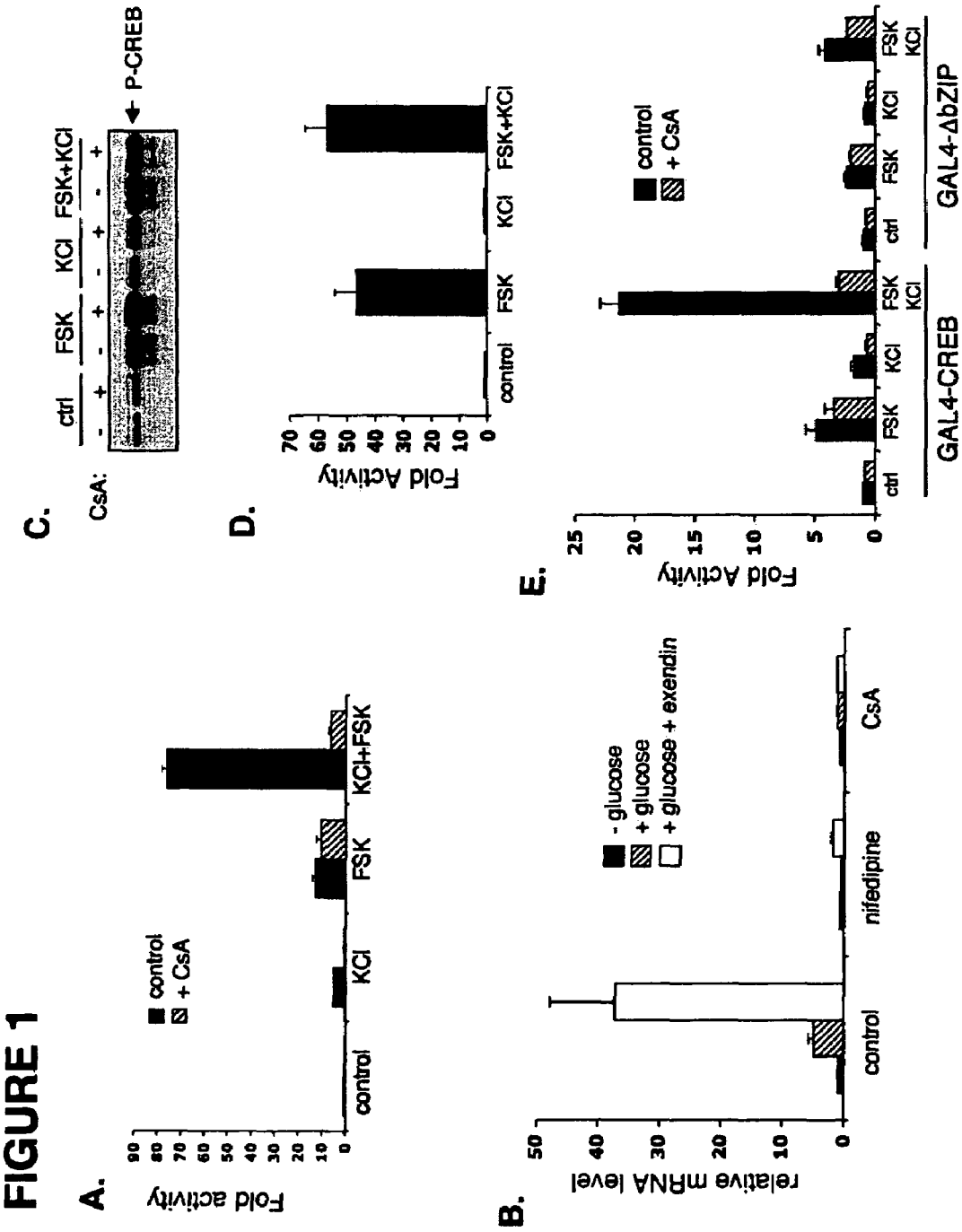
FIGS. 1A-1E demonstrate that the CREB bZIP domain is required for cooperativity between cAMP and calcium signals. Specifically, FIG. 1A summarizes the results of a transient transfection assay of HIT insulinoma cells transfected with the CREB-dependent EVX-1 luciferase reporter. Cells were treated with KCl (45 mM) and/or forskolin (10 nM) for six hours as indicated. The effect of treatment with the calcineurin inhibitor, Cyclosporine A (CsA, 5 FM) is shown.

In accordance with the present invention, there are provided methods of screening test compounds to determine if such compounds are capable of enhancing islet cell activity and/or survival. Invention methods comprise determining the effect of test compound on one or more of:
the transport of a Transducer Of Regulated CREB (TORC) from the cytoplasm into the nucleus of an islet cell,
the kinase activity of a snf1-like kinase,
the interaction between a Transducer Of Regulated CREB (TORC) and a member of the 14-3-3 family of proteins, or
the level of phosphorylation of a Transducer Of Regulated CREB (TORC),
wherein one or more of the following, in the presence of test compound, is indicative of a compound which is capable of enhancing islet cell activity and/or survival:
enhanced transport of TORC from the cytoplasm into the nucleus of an islet cell, reduced kinase activity of the snf1-like kinase,
disruption of the interaction between TORC and a member of the 14-3-3 family of proteins, or
a reduction in the level of phosphorylation of TORC.

In accordance with one embodiment of the present invention, there are provided methods of screening test compounds to determine if such compounds are capable of enhancing islet cell activity and/or survival. Invention methods comprise determining the effect of test compound on the transport of a Transducer Of Regulated CREB (TORC) from the cytoplasm into the nucleus of an islet cell, wherein enhanced transport of TORC from the cytoplasm into the nucleus of an islet cell in the presence of test compound is indicative of a compound which is capable of enhancing islet cell activity and/or survival.

As employed herein, "islet cell activity" refers to the role islet cells play in the regulation of blood glucose levels. For example, beta islet cells produce and secrete insulin, which acts to decrease blood glucose levels by mediated cell absorption of glucose. Failure (e.g., cell death) of beta islet cells (and hence, the ability to produce insulin) has been implicated, for example, in the development of type II diabetes in obese individuals. Similarly, in type I diabetes, beta islet cells are depleted by autoimmune attack thereon. In contrast to the role of beta islet cells, alpha islet cells secrete glucagon, which increases blood glucose levels by stimulation of cellular production and release of glucose.

As employed herein, "survival" of islet cells refers to the continued viability of islet cells whether in native host tissue, or upon transplantation, the ability of islet cells to resist the factors which lead to cell death (and hence type II diabetes), the ability of islet cells to resist the factors which lead to autoimmune attack thereon, and the like.

As readily recognized by those of skill in the art, a number of Transducers Of Regulated CREB (TORCs) are known. Indeed, several isoforms have been identified (e.g., TORC1, TORC2, TORC3, and the like). TORCs have been shown to accumulate in the nucleus in response to increased intracellular calcium or cAMP, contributing to activation of CRE-dependent transcription.

In accordance with another embodiment of the present invention, there are provided methods of screening test compounds to determine if such compounds are capable of enhancing islet cell activity and/or survival. Invention methods comprise determining the effect of test compound on the kinase activity of a sucrose-nonfermenting-1 (snf1)-like protein kinase, wherein reduced kinase activity of the snf1-like kinase in the presence of said test compound is indicative of a compound which is capable of enhancing islet cell activity and/or survival.

As readily recognized by those of skill in the art, a number of snf1-like kinases are known, e.g., SIK1, SIK2, SIK3, and the like. These SIK proteins are serine/threonine kinases and are members of an AMP-activated protein kinase family. Salt-inducible kinase-1 (SIK1) was first isolated from the adrenal glands of rats on a high salt diet. SIK1 is primarily expressed in rat adrenal gland and may play a role in regulating steroidogenic gene expression. SIK2 and SIK3 were subsequently cloned and exhibit adipose-specific and ubiquitous expression, respectively. SIK2 phosphorylates cytoplasmic TORC at Ser171, thereby mediating the phosphate-dependent interaction of TORC and 14-3-3. This results in a repression of TORC translocation to the nucleus and a decrease in TORC-mediated CREB activity.

In accordance with still another embodiment of the present invention, there are provided methods of screening test compounds to determine if such compounds are capable of enhancing islet cell activity and/or survival. Invention methods comprise determining the effect of test compound on the interaction between a Transducer Of Regulated CREB (TORC) and a member of the 14-3-3 family of proteins, wherein disruption of the interaction between TORC and a member of the 14-3-3 family of proteins in the presence of test compound is indicative of a compound which is capable of enhancing islet cell activity and/or survival.

As readily recognized by those of skill in the art, 14-3-3 proteins comprise a family of phosphoserine/phosphothreonine binding proteins. At least seven isoforms of 14-3-3 ($\beta$, $\gamma$, $\in$, $\sigma$, $\xi$, $\tau$, and $\eta$) have been described in mammalian cells. 14-3-3 proteins form homodimers and heterodimers capable of interacting with other cellular proteins. The phosphoserine/phosphothreonine-binding activity of 14-3-3 enables these molecules to interact with a wide variety of other cellular proteins and thereby contribute to the regulation of a number of important cellular processes (e.g., metabolism, apoptosis, cell cycle control, and the like). 14-3-3 proteins repress TORC translocation to the nucleus via a phosphate-dependent interaction with TORC. Disruption of such interactions (e.g, via dephosphorylation of TORC) allows TORC to translocate to the nucleus and increase TORC-mediated CREB activity.

In accordance with a further embodiment of the present invention, there are provided methods of screening test compounds to determine if such compounds are capable of enhancing islet cell activity and/or survival. Invention methods comprise determining the effect of test compound on the level of phosphorylation of a Transducer Of Regulated CREB (TORC), wherein a reduction in the level of phosphorylation of TORC in the presence of test compound is indicative of a compound which is capable of enhancing islet cell activity and/or survival.

There are a variety of positions on the TORCs which can be phosphorylated, e.g., at a position comparable to Ser171 of TORC2, and the like.

In accordance with a further embodiment of the present invention, there are provided methods of screening test compounds to determine if such compounds are capable of promoting CREB-mediated gene expression in islet cells. Invention methods comprise determining the effect of test compound on one or more of:
the transport of a Transducer Of Regulated CREB (TORC) from the cytoplasm into the nucleus of an islet cell,
the kinase activity of a snf1-like kinase,
the interaction between a Transducer Of Regulated CREB (TORC) and a member of the 14-3-3 family of proteins, or
the level of phosphorylation of a Transducer Of Regulated CREB (TORC),
wherein one or more of the following, in the presence of test compound, is indicative of a compound which is capable of promoting CREB-mediated gene expression in islet cells:
enhanced transport of TORC from the cytoplasm into the nucleus of an islet cell, reduced kinase activity of the snf1-like kinase,
disruption of the interaction between TORC and a member of the 14-3-3 family of proteins, or
a reduction in the level of phorphorylation of TORC.

In accordance with still another embodiment of the present invention, there are provided methods of screening test compounds to determine if such compounds are capable of promoting CREB-mediated gene expression in islet cells. Invention methods comprise determining the effect of test compound on the transport of a Transducer Of Regulated CREB (TORC) from the cytoplasm into the nucleus of an islet cell, wherein enhanced transport of TORC from the cytoplasm into the nucleus of an islet cell in the presence of test compound is indicative of a compound which is capable of promoting CREB-mediated gene expression in islet cells.

In accordance with yet another embodiment of the present invention, there are provided methods of screening test compounds to determine if such compounds are capable of promoting CREB-mediated gene expression in islet cells. Invention methods comprise determining the effect of test compound on the kinase activity of a snf1-like kinase, wherein reduced kinase activity of the snf1-like kinase in the presence of said test compound is indicative of a compound which is capable of promoting CREB-mediated gene expression in islet cells.

In accordance with another embodiment of the present invention, there are provided methods of screening test compounds to determine if such compounds are capable of promoting CREB-mediated gene expression in islet cells. Invention methods comprise determining the effect of test compound on the interaction between a Transducer Of Regulated CREB (TORC) and a member of the 14-3-3 family of proteins, wherein disruption of the interaction between TORC and a member of the 14-3-3 family of proteins in the presence of test compound is indicative of a compound which is capable of promoting CREB-mediated gene expression in islet cells.

In accordance with still another embodiment of the present invention, there are provided methods of screening test compounds to determine if such compounds are capable of promoting CREB-mediated gene expression in islet cells. Invention methods comprise determining the effect of test compound on the level of phosphorylation of a Transducer Of Regulated CREB (TORC), wherein a reduction in the level of phorphorylation of TORC in the presence of test compound is indicative of a compound which is capable of promoting CREB-mediated gene expression in islet cells.

In accordance with yet another embodiment of the present invention, there are provided methods of screening test compounds to determine whether such compounds effect transport of a Transducer Of Regulated CREB (TORC) from the cytoplasm into the nucleus of an islet cell. Invention methods comprise determining the effect of test compound on the transport of TORC from the cytoplasm into the nucleus of an islet cell.

As readily recognized by those of skill in the art, a test compound which effects transport of TORC from the cytoplasm into the nucleus of a cell can either enhance such transport, or reduce such transport.

There are a variety of cells in which TORC transport is important, e.g., islet cells (e.g., alpha and beta islet cells), muscle cells (e.g., cardiac muscle), liver cells, adipose cells, neuronal cells, and the like.

In accordance with a further embodiment of the present invention, there are provided methods of screening test compounds to determine whether such compounds effect the kinase activity of an snf1-like kinase. Invention methods comprise determining the effect of test compound on the kinase activity of an snf1-like kinase.

As readily recognized by those of skill in the art, a test compound which effects the kinase activity of an snf1-like kinase can either enhance such activity, or reduce such activity.

In accordance with another embodiment of the present invention, there are provided methods of screening test compounds to determine whether such compounds effect the interaction between a Transducer Of Regulated CREB (TORC) and a member of the 14-3-3 family of proteins. Invention methods comprise determining the effect of test compound on the interaction between TORC and a member of the 14-3-3 family of proteins.

A test compound which effects the interaction between TORC and a member of the 14-3-3 family of proteins can either enhance or disrupt such interaction.

In accordance with still another embodiment of the present invention, there are provided methods of screening test compounds to determine whether such compounds effect the level of phosphorylation of a Transducer Of Regulated CREB (TORC). Invention methods comprise determining the effect of test compound on the level of phosphorylation of TORC. Optionally, the above-described method can be carried out in the further presence of a phosphatase such as calcineurin.

As readily recognized by those of skill in the art, a test compound which effects the level of phosphorylation of TORC can either enhance or reduce the level of phosphorylation of TORC.

In accordance with a further embodiment of the present invention, there are provided compounds identified by any of the above-described methods.

In accordance with yet another embodiment of the present invention, there are provided methods for enhancing islet cell activity and/or survival, said method comprising enhancing the transport of a Transducer Of Regulated CREB (TORC) from the cytoplasm into the nucleus of an islet cell.

As readily recognized by those of skill in the art, transport of TORC from the cytoplasm into the nucleus of an islet cell can be enhanced in a variety of ways, e.g., by blocking activation of SIK2 (or related family members), by disrupting the interaction between TORC and a member of the 14-3-3 family of proteins, by dephosphorylating TORC, and the like. As readily recognized by those of skill in the art, this can be accomplished in a variety of ways, e.g., by administering an effective amount of a compound identified by any of the above-described methods to a subject in need thereof.

Figure 8:
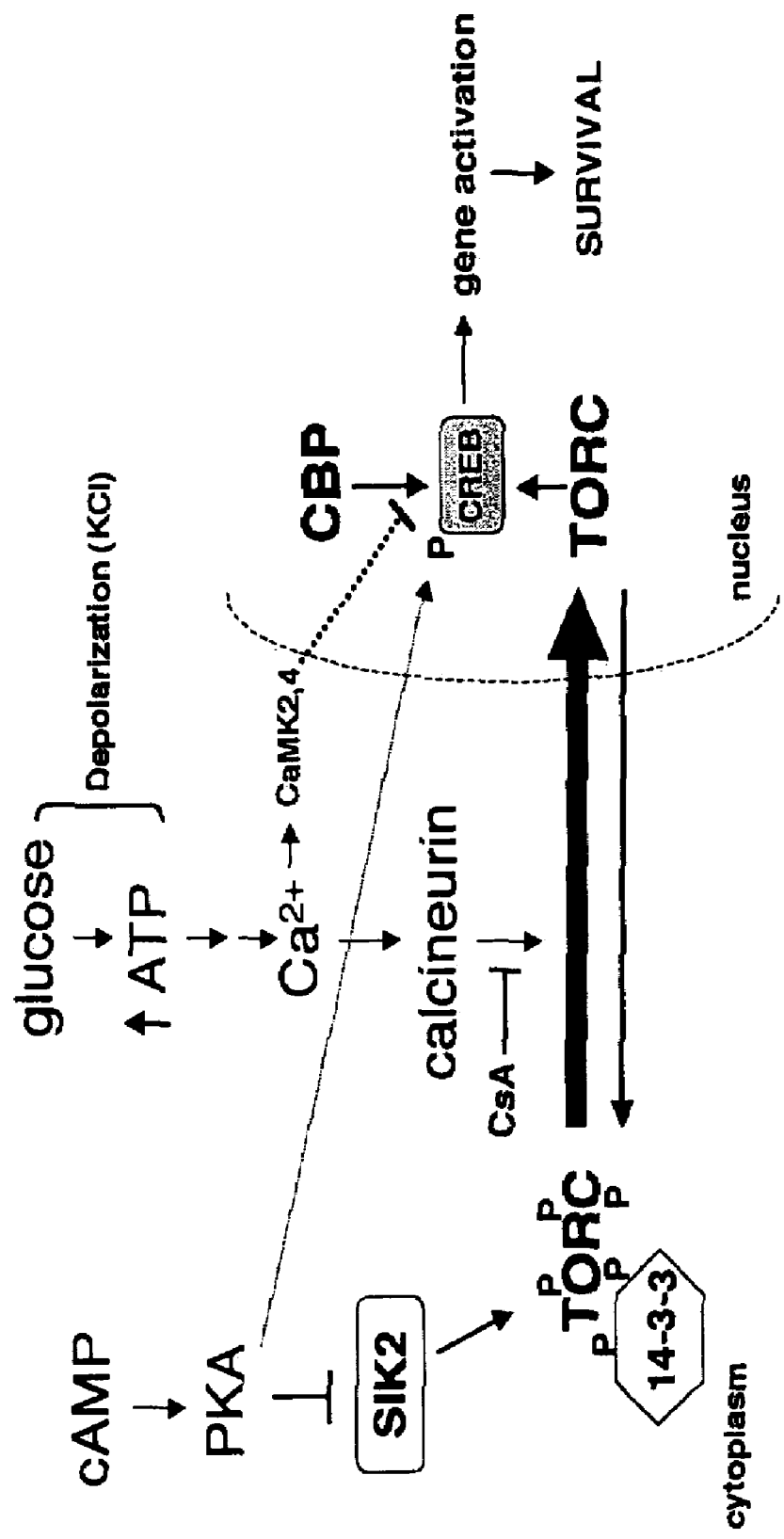
FIG. 8 presents a model for cooperative induction of cellular genes in response to cAMP and calcium signals in insulin producing beta cells. SIK2 (and related family members) promotes Ser171 phosphorylation and association of TORC2 with 14-3-3 proteins. cAMP and calcium agonists activate TORC2 via cooperative effects on TORC2 dephosphorylation and nuclear entry. cAMP inhibits TORC2 associated activity of SIK2 and related family members, whereas calcium signals promote calcineurin dependent dephosphorylation of TORC2. Nuclear TORC2 stimulates CREB activity via an interaction with the bZIP domain of CREB. In parallel, cAMP stimulates phosphorylation of CREB at Ser133 and recruitment of the histone acetylase CBP to the promoter.

Described herein is a new pathway that operates in parallel with the histone acetylase coactivators CBP/P300 to activate cellular genes in response to cAMP and calcium signals (see FIG. 8). Despite their cooperative effects on cellular gene expression, calcium and cAMP do not promote either CREB Ser133 phosphorylation or CREB:CBP complex formation in a synergistic fashion. Indeed, knockin mice with point mutations in the KIX domain of CBP and P300 that disrupt the CREB interaction display only modest changes in cAMP responsiveness (Kasper et al., 2002), consistent with the existence of a distinct pathway that also mediates cellular gene activation via CREB.

The CREB:TORC pathway is activated in response to extracellular signals; it does not require Ser133 phosphorylation but rather operates through the CREB bZIP domain, a region which has been found to contribute functionally to cAMP and calcium signaling in excitable cells (Bonni et al., 1995b; Sheng et al., 1991). The importance of this domain for target gene activation may explain in part why CREB homodimerizes selectively with related family members (CREB1, ATF1, CREM) and not with other bZIP proteins (Newman and Keating, 2003).

TORCs fulfill a number of criteria for coactivators that mediate cooperativity between cAMP and calcium signals. First, they stimulate CREB activity through a bZIP domain interaction; point mutants that disrupt this interaction compromise cellular responses to both cAMP and calcium agonists. Indeed, TORC2 is recruited to the promoter in a signal-dependent manner, and knockdown of TORC2 disrupts induction of CREB target genes in response to cAMP.

Disrupting the CREB:CBP interaction by mutagenesis of the Ser133 phosphoacceptor site in CREB compromises cAMP inducibility, but has no effect on either the costimulatory actions of cAMP and calcium second messengers nor on the ability of CsA to block this cooperativity. The importance of the bZIP domain but not phospho(Ser133) for calcium dependent transcription may explain in part why CREB remains active in this setting even though calcium signals trigger its phosphorylation at sites (Ser142 and 143) that are inhibitory for the CREB:CBP interaction (Kornhauser et al., 2002).

Without wishing to be bound by any theory, the putative mechanism underlying TORC activation is reminiscent of the cytoplasmic family of NFAT transcription factors (Crabtree and Olson, 2002; Hogan et al., 2003). Indeed, TORCs and NFATs are both maintained in the cytoplasm under basal conditions via phosphorylation at sites that promote an interaction with 14-3-3 proteins. Both sets of proteins are dephosphorylated in response to calcium signals via a direct association with the calcium dependent phosphatase calcineurin. Indeed, the calcineurin binding site in TORC contains a sequence (TORC2: amino acid 248-PGINIF; SEQ ID NO:2) that resembles the consensus calcineurin interaction motif identified for NFATs (PXIXIT; SEQ ID NO:3) (Aramburu et al., 1998), although the importance of this site for the TORC: calcineunin interaction was not addressed. Like NFATs, binding sites for calcineunin and 14-3-3 proteins on TORC appear to cluster within a regulatory domain that also contains nuclear import and export signals. The Ser171 SIK2 phosphorylation site in TORC2 is part of a potential mode 2 binding site for 14-3-3 (RXXXpSXP; SEQ ID NO:4). Based on its proximity to TORC2 NLS motifs (aa. 1-147), Ser171 is believed to perform a gatekeeper function, masking NLS motifs from the import machinery in a manner comparable to NFAT (Okamura et al., 2000) and other proteins. It is of note that TORC2 is also phosphorylated at numerous additional sites in addition to Ser171, and these may also contribute to TORC2 regulation.

cAMP and calcium promote TORC2 dephosphorylation cooperatively in beta cells via their effects on TORC2 associated Ser/Thr kinase and phosphatase activities. Treatment with the calcineurin inhibitor CsA reverses the effects of cAMP and calcium on TORC dephosphorylation and CREB target gene activation. Conversely, cAMP promotes TORC activation by disrupting the TORC associated ser/thr protein kinase SIK2 (and related family members).

SIK2 is a member of a larger family of at least 13 AMPK (AMP-activated protein kinase) related kinases that includes 3 SIKs (SIK1, SIK2, SIK3), 4 MARKs (MARK-1, MARK-2, MARK-3/PAR1A, MARK-4) as well as AMPK-αd, and AMPK-α2. The AMPK related family of kinases is activated through phosphorylation by LKB-1, a tumor suppressor that is mutated in Peutz Jehgers syndrome (PJS), a familial disorder characterized by multiple colon polyps and an increased incidence of colon and other cancers (Carling, 2004; Lizcano et al., 2004; Shaw et al., 2004; Woods et al., 2003). LKB-1 phosphorylates AMPK family members, including SIK2, at a conserved Thr in the T-loop that stimulates their kinase activity more than 50-fold (Carling, 2004). Loss of LKB-1 would be predicted to activate CREB target gene expression by reducing levels of SIK2 (or related family member)-dependent TORC2 phosphorylation. Remarkably, TORC1 has been described as part of a fusion protein with the Notch coactivator mastermind like 2 (MAML2) that arises from a chromosomal translocation in mucoepidermoid carcinomas of the salivary and bronchial glands (Enlund et al., 2004; Tonon et al., 2003). Notably the TORC1-MAML2 fusion gene contains the CREB binding domain of TORC1 (aa. 1-42) but lacks the central TORC regulatory domain that is phosphorylated by SIK2 (or related family members). Correspondingly, the TORC-MAML2 fusion gene is constitutively nuclear and displays high basal activity on CREB target genes (Conkright et al., 2003a; Tonon et al., 2003). The results presented herein are consistent with the proposed mechanism whereby the loss of LKB-1 activity in PJS similarly promotes oncogenic transformation in part by activating the CREB: TORC pathway.

Elevations in circulating glucose and GLP-1 promote islet survival in part through their cooperative effects on CREB activity. Calcineurin inhibitors such as FK506 and CsA have been found to cause β cell failure and diabetes with high frequency in organ transplant recipients receiving chronic immunosuppressive therapy (Al-Uzri et al., 2001; Filler et al., 2000). Based on their ability to interfere with glucose and incretin signaling to TORC, these calcineurin inhibitors may promote islet cell death in part by blocking CREB target gene activation. In this regard, the development of specific SIK antagonists is expected to improve islet cell function and offer useful therapy for insulin resistant individuals.

The effects of SIK2 and related family members on cellular gene regulation by CREB is likely to extend to other electrically excitable tissues. Both SIKs and TORCs are highly expressed in the brain, for example, an area where CREB appears to function in higher order processes such as learning and memory. Targeted disruption of SIK and TORC genes in these and other tissues will enable one to mediate responses to extracellular signals.

The invention will now be described in greater detail with reference to the following non-limiting examples. See also Screaton et al., 2004 and Koo et al., 2005, the entire contents of each of which is hereby incorporated by reference.

EXAMPLES

Chemicals:
LMB and Exendin-4 (Sigma, Saint Louis, Mo.) were used at 10 ng/ml and 10 nM, respectively. Nifedipine (10 uM), Cyclosporine A (CsA, 5 µM) and okadaic acid, (OA, 100 nM) were from Calbiochem (San Diego, Calif.). $^{32}$P orthophosphate in 0.02 N HCl was from ICN.

Cell Culture:
HEK293T cells were cultured in DME+10% FBS+pen/strep. HIT-T15 cells were cultured in F12/K medium with 10% HS+2.5% FBS+pen/strep. MIN6 were cultured in DME with 10% FBS+pen/strep and 50 µM beta-mercaptoethanol.

Quantitative PCR:
Cells were treated with cAMP agonist (Forskolin, 10 µM) and KCl (45 mM) or vehicle control. For glucose experiments, MIN6 cells were starved overnight in DME containing 2.75 mM glucose plus 16 mM mannitol and 10% FBS. The next day the medium was changed for the indicated times+ inhibitor. Total RNA from treated MIN6 or HIT cells was extracted using an RNeasy mini-kit (Qiagen, Valencia, Calif.). 500 ng-1 µg of total RNA was used for generating cDNA with Superscript II enzyme (Invitrogen, Carlsbad, Calif.). cDNAs were analyzed by quantitative PCR using SYBR green PCR kit and an ABIPRISM 7700 Sequence detector (Perkin Elmer, Foster City, Calif.). All PCR data for CREB target NR4A2 (Conkright et al., 2003b) was normalized to ribosomal L32 or 36B4 expression in the corresponding sample.

Antisera, Western Blot Analysis, Immunoprecipitation and GST-Pulldown:
Rabbit pan-TORC (raised against 1-42 of human TORC1) and TORC2 selective rabbit polyclonal antiserum (raised against amino acids 454-607 of mouse TORC2) were generated as previously described (Conkright et al., 2003a)). Whole cell protein was extracted from cultured HEK293T, HIT, and MIN6 cells in Laemmli SDS sample buffer. Alternatively, whole cell protein was extracted from liver tissue or primary hepatocytes in SDS-urea-lysis buffer. 10-20 µg of protein was separated by 8, 10 or 4-20% SDS-PAGE and transferred to PVDF membrane (Millipore Corp., Bedford, Mass.). Alternatively, 50-100 µg of protein was loaded onto a 6% SDS-polyacrylamide gel and blotted onto nitrocellulose membrane (Schleicher & Schuell, Keene, N.H.). Chromatin immunoprecipitation and co-immunoprecipitation experiments were performed as described (Conkright et al., 2003a).

Western blot analyses were conducted on whole cell, cytoplasmic and nuclear extracts with the following rabbit polyclonal antisera: phospho (Ser133) specific affinity purified 5322 and phospho (Ser133) specific antibody from Rockland Immunochemicals, Gilbertsville, Pa.), non-discriminating CREB (244), phosphor (Ser171) CREB, TORC2, pan-TORC, SIK1 and SIK2. 14-3-3 and Hsp90 antibodies were from Santa Cruz (Santa Cruz, Calif.). FLAG-M2 (Sigma) and GAL4 (Santa Cruz) monoclonal antibodies were used at 1:2000 and 1:1000 dilutions, respectively. For quantitative western blotting, goat anti-mouse-800 nm fluorophore conjugate to detect FLAG-M2 was used at 1:40,000 dilution according to manufacturer's instructions (Licor) prior to analysis using the Odyssey detection system. GST-pulldowns were performed as described (Asahara et al., 2001).

For immunoprecipitation, whole cell protein was extracted from liver tissue, primary hepatocytes, or mouse hepal c1c7 in lysis buffer (20 mM Tris, pH 7.6, 150 mM NaCl, 1 mM EDTA, 1 mM EGTA, 1% Trition X-100, 2.5 mM β glycerol pyrophosphate, 1 mM NaVO$_4$, 1 mM NaF and 1 mM DTT. Immunoprecipitation of HA-TORC2 was performed according to manufacturer's instructions.

DNA Plasmid Constructs:

Site-specific mutant TORC and CREB cDNAs were generated using the Quickchange protocol (Stratagene, La Jolla, Calif.) or by PCR-mediated restriction fragment recombination and then verified by sequencing. Protein expression of these constructs was evaluated by Western blot and immunofluorescence analysis using anti-Flag or anti-GAL4 antibodies. TORC2 RNAi plasmid has been described (Conkright et al., 2003a).

SIK1 promoter sequences containing residues −425 to −76 were amplified by PCR from mouse genomic DNA and inserted into pXP2 Luc reporter vector to genenate mSIK1 (−425/+76) Luc construct. PEPCK (−549/+49) Luc reporter, AOX Luc reporter, PGC-1 expression construct, and nonspecific control pU6-US construct have been described previously (see Koo et al., 2004). pU6-RNAi plasmids were generated as described previously. The coding sequence from 468 to 488 (GGGGCAGTTGTTTAGACTGCC; SEQ ID NO:5) was used for targeting mouse TORC2, and the coding sequence from 355 to 376 (GGGCACTTGAGTGAAAAC-GAGG; SEQ ID NO:6) was used for targeting mouse/rat SIK1.

Transient Reporter Assays:

HEK293T, HIT or PC 12 cells were co-transfected with EVX or GAL4-LUC reporter plasmid, RSV-beta galactosidase and FLAG-TORC and/or SIK2 expression plasmids overnight using Lipofectamine 2000 (Invitrogen, Carlsbad, Calif.). DNA/lipid complexes were washed the next day and extracts prepared 24 h (293T and PC 12) or 40 hr (HITs) after transfection. 45 mM KCl and/or 10 µM forskolin were added 6 hr prior to harvest and 7 hr hour after CsA treatment where indicated. Luciferase values were normalized to β-gal activity from co-transfected RSV-beta galactosidase activity in the corresponding sample.

In Vitro and In Vivo Phosphorylation Assays:

HIT and MIN6 insulinoma cells were transfected with Flag-tagged TORC1, TORC2, or TORC3 expression vector. In vivo: after 40 h, transfected cells were incubated with phosphate-free Dulbecco's modified Eagle medium containing 10% dialyzed serum and 1 mCi of [$^{32}$P]orthophosphate/ ml. After 4 h, cells were washed with ice cold Tris-buffered saline, and harvested in either boiling SDS or RIPA lysis buffer (0.1 % SDS, 1% Triton X-100, 0.5% deoxycholate, 50 mM Tris [pH 8.0], 1 mM EDTA, 100 mM NaCl) containing a cocktail of phosphatase inhibitors (50 mM sodium fluoride, 1 mM sodium fluoride, 1 mM sodium vanadate) plus 20 µg RNAse and 1 mM DTT. Samples were diluted to IX RIPA (for boiling SDS samples) and immunoprecipitated after preclearing with Staph A using anti-Flag agarose (Sigma). In vitro: FLAG-TORC immune complexes were collected on Protein A-agarose, extensively washed and then subjected to a kinase assay by incubation with 50 µCi γ-ATP and 10 µM unlabeled ATP at 37° C. for 30 minutes in 50 mM HEPES, pH 7.4, 10 mM MgCl$_2$, 1 mM KCl. The reaction was washed once with reaction buffer and stopped by boiling in 2× Laemmli sample buffer.

Indirect Immunofluorescence:

Human ATYBI fibroblasts on coverslips were fixed with 4% paraformadehyde in PBS for 20 min. For staining of transient transfectants, cells were fixed 40 h after transfection. Fixative was quenched with 0.1 M glycine prior to permeabilization with 0.1% TX-100/PBS for 2 min. Nonspecific sites were blocked with 3% BSA/PBS prior to staining with anti-FLAG M2 monoclonal antibody (1:2000) or anti-pan TORC antiserum (1:1000) in 3% BSA/PBS. Antigens were revealed by incubation with donkey anti-mouse or anti-rabbit Alexa 488- or Cy3-conjugated secondary antibody (Molecular Probes, Eugene, Oreg., Jackson Immunochemicals) prior to mounting in Vectashield with DAP1 counterstain (Vector Labs). All steps were performed at 25° C.

Mass Spectrometry and Phosphorylation Site Determination:

Proteins resuspended in 8 M Urea, 100 mM Tris pH 8.5 were subjected to reduction and alkylation using 5 mM TCEP (Sigma) and 10 mM IAM (Sigma) respectively. Protein mixtures were then divided into three equal aliquots and diluted to 2 M Urea (4 M for Subtilisin) followed by digestion with 0.01 µg/µl Trypsin (Promega), 0.005 µg/µl Elastase and 0.005 µg/µl Subtilisin (Roche) (MacCoss et al., 2002). The resulting peptide mixture was then analyzed by a 7 step MudPIT analysis essentially as described (Link et al., 1999), except proteins were displaced from the SCX to the RP column using the following salt step gradients (1) 0% (2) 0-10% (3) 10-25% (4) 25-50% (5) 50-65% (6) 65-80% and (7) 80-100% of Buffer-A to Buffer-C. Peptides were eluted from the RP column into the mass spectrometer using a linear gradient of 15-55% of Buffer-A to Buffer-B. Mobile-phase buffers were, for Buffer-A, 95% H$_2$O, 5% acetonitrile, 0.1% formic acid; for Buffer-B, 20% H$_2$O, 80% acetonitrile, 0.1% formic acid; for Buffer-C, 500 mM NH$_4$OAc, 5% acetonitrile, and 0.1% formic acid. Tandem mass spectra were searched against the most recent versions of the predicted rat, mouse, and human proteins, to which common contaminants, such as keratin and trypsin, were added using a modified version of the PEP_PROB algorithm. Search results were filtered and grouped using DTA-Select (Tabb et al., 2002). For phosphorylation analysis a subset database was generated which contained only the proteins that were identified. The MSMS data were then researched against this subset database for the modification of +80 on Ser/Thr/Tyr. The spectra containing the prominent 98-Da neutral loss were also searched against the subset database by using a modified version of SEQUEST that considers the unique MS/MS fragmentation patterns of phosphorylated Ser and Thr containing peptides (MacCoss et al., 2002). Only phosphorylation sites that were matched by multiple tandem mass spectra representing sequences of different molecular weights (from the non-specific enzymes used in the digest) were called matches. Tandem mass spectra matched to phosphorylated peptides were manually validated.

Culture of Primary Hepatocytes:

Rat primary hepatocytes were prepared from 200-300g of Sprague-Dawley rats by collagenase perfusion method as described previously (see Koo et al., 2004). $1 \times 10^6$ cells were plated in 6 well plates with medium 199 (Invitrogen, Carlsbad, Calif.) supplemented by 10% FBS, 10 units/ml penicillin, 10 μg/ml streptomycin, and 10 nM dexamethasone for 3-6 hours. After attachment, cells were infected with adenoviruses for 16 hours. Subsequently, cells were maintained in medium 199 without FBS and dexamethasone for 24 hours (for cDNA expression adenoviruses) or 48 hours (for RNAi adenoviruses) and 10M forskolin or 100 nM glucagon for 2 hours unless noted otherwise. For experiments with cycloheximide, 10 μg/ml cycloheximide was added 30 minutes prior to the addition of 100 nM glucagon.

Transfection Assays:

Human hepatoma HepG2 cells were maintained with Ham's F12 medium supplemented with 10% FBS (Invitrogen, Carlsbad, Calif.). For transfection, Fugene 6 reagent (Roche Applied Science) was used according to the manufacture's instructions. Each transfection was performed with 100 ng of luciferase construct, 50 ng of beta galactosidase expression plasmid and 15 ng of expression vector for TORC2, 50 ng of expression vector for ACREB, 50ng of expression vector for SIK1, or 50 ng of expression vector for PKA catalytic subunit. If necessary, the empty pcDNA3 vector (Invitrogen, Carlsbad, Calif.) was used for adding a constant amount for each transfection. 48 hours post transfection, cells were treated with either DMSO or 10M Forskolin (Sigma, St. Louis, Mo.) for 4 hours and were harvested for luciferase assays. The luciferase activity was normalized by beta galactosidase activity. For transfection with AOX reporter constructs, 100 ng of luciferase construct, 50 ng of beta galactosidase expression plasmid and 5 or 15 ng of expression vector for PGC-1α or 50 ng of expression vector for SIK1 were used.

Recombinant Adenoviruses:

Adenoviruses expressing GFP only and unspecific control were described previously (see Koo et al., 2004). Adenoviruses for SIK1, SIK2, as well as wild-type and Ser171 Ala TORC2 expression were generated by homologous recombination between adenovirus bacTORC2, SIK1 or SIK2 were generated by homologous recombination between adenovirus backbone vector pAD-Easy and linearized transfer vector pAD-Track that contains mouse TORC2 cDNA, rat SIK1 cDNA or mouse SIK2 cDNA sequences, respectively. Adenoviruses for TORC2 RNAi and SIK1 RNAi were generated by homologous recombination between adenovirus backbone vector pAD-Easy and linearized transfer vector pAD-Track that contains U6-TORC2 RNAi or U6-SIK1 RNAi sequences, respectively. The virus contained the cDNA that express GFP under the control of CMV promoter for monitoring the infection efficiency. For animal experiments, viruses were purified by CsCl method and dialyzed against PBS buffer containing 10% glycerol before the injection.

Animal Experiments:

Male 7-week-old C57BL6 mice were purchased from Harlan and maintained in regular chow under the 12-h light-dark cycle. $0.5 \times 10^9$ plaque-forming units per recombinant adenovirus was delivered by a systemic tail vein injection to mice that were anaesthetized with Iso-Flurane. For measuring fasting blood glucose level, animals were fasted for 16 hours with free access to water. Blood glucose was monitored at the end of each fasting period for 5 to 9 days. Liver tissues were collected at the end of experiments and immediately frozen in liquid nitrogen. Western blots were performed with GFP antibody to check the relative infection. For the localization of TORC2 in liver, mice with adenovirus for mouse TORC2 were injected intraperitoneally with either 5 Ag/kg body weight of glucagon, 1 unit/kg body weight of insulin on PBS.

Metabolites:

Blood glucose level was monitored from tail vain blood using an automatic glucose monitor (One Touch, Lifescan, Fremont, Calif.). Plasma insulin levels were determined using a commercial insulin enzyme-linked immunosorbent assay kit (ALPCO Diagnostics, Windham, N.H.).

Immunostaining:

Formalin-fixed, paraffin-embedded liver sections (5 μm) were deparaffinized in two changes of xylenes and hydrated to $H_2O$ by successive 5-min washes in 100% ethanol, 90% ethanol, 70% ethanol, and distilled $H_2O$. Antigen unmasking was performed by microwaving slides for 10 min in 1 mM EDTA. After cooling to room temperature, slides were rinsed twice in PBS. Slides were then incubated with PBS and 5% normal donkey serum for 20 min. After incubation, slides were incubated with the following rabbit antibodies for 60 mm at room temperature: antiTORC2 (1:1600), anti-CREB (244, 1:600) and anti-pCREB (5322, 1:500). After antibody incubation and extensive washes, slides were incubated with donkey anti-rabbit Cy3 at 1:600 dilutions for 45 mm at room temperature. Slides were then washed three times in PBS and mounted with coverslips with the use of Vectashield mounting media containing 4',6-diamidino-2-phenylindole (DAPI).

Chromatin IP:

Mice were injected intraperitoneally with either 5 μg/kg body weight of glucagon or 1 unit/kg body weight of insulin for 10 minutes. Subsequently, nuclear isolation, chromatin crosslinking and ChiP assays were performed as described (see Screaton et al., 2004). Precipitated DNA fragments were analyzed by quantitative polymerase chain reaction (Q-PCR) amplification using primers directed against the mouse promoters listed in figure legends. For analysis of mouse SIK1 promoter, SV40-transformed mouse hepatocytes were grown to 90% confluence, and used for ChiP assays as described (see Screaton et al., 2004). SV40-transformed mouse hepatocytes were grown to 90% confluence, and ChiP assays were performed. Precipitated DNA fragments were analyzed by polymerase chain reaction (PCR) amplification using primers directed against the mouse SIK1 promoter or beta actin coding region as negative control.

In Vitro Kinase Assay:

Recombinant GST-TORC2 (161 -181) wild-type and Ser171 Ala proteins were phosphorylated in vitro with 100 mU purified AMPK (AMP-activated protein kinase) (Upstate Biotech) ±300 μM AMP according to the manufacturer's instructions. Following 15 mm. incubation with $\gamma$-$^{32}$P-ATP, relative $^{32}$P incorporation was measured by scintillation. GST substrates and SAMS peptide were used at 3 μM in each reaction.

Example 1

A Calcineurin Sensitive Cofactor Promotes Cooperativity between cAMP and Calcium Pathways Hamster insulinoma (HIT) cells were employed to test the relative effects of cAMP and calcium signals on CREB activity. Opening of voltage-sensitive L-type calcium channels in response to KC1 depolarization induced the CREB-dependent EVX-1 promoter (Conknight et al., 2003b) 5-fold in HIT cells, whereas addition of cAMP agonist stimulated the reporter 10-fold (see FIG. 1A). Co-stimulation with both forskolin and KC1 stimulated CREB activity 80-fold, demonstrating the cooperative effects of cAMP and calcium pathways on CREB target gene expression in these cells. Pre-treatment with the calcineurin inhibitor cyclosporine A (CsA) blocked cooperativity between cAMP and calcium pathways, indicating that calcineurin performs an important role in modulating CREB activity. Consistent with the effects of calcium channel activity on the EVX-1 promoter, treatment with high glucose (20 mM) induced the expression of the endogenous CREB target gene NR4A2 5-fold in MIN6 insulinoma cells; and co-stimulation with glucose plus exendin-4, an analogue of the incretin hormone GLP-1, enhanced NR4A2 mRNA levels 35-fold (see FIG. 1B). In keeping with the importance of calcium entry for CREB target gene activation, treatment with the calcium channel inhibitor nifedipine blocked the effect of glucose on NR4A2 mRNA accumulation. Cooperative induction of NR4A2 mRNA levels by glucose and exendin-4 was also calcineurin-dependent; addition of CsA disrupted the increase in NR4A2 mRNA gene expression by both stimuli (see FIG. 1B).

Figure 9:
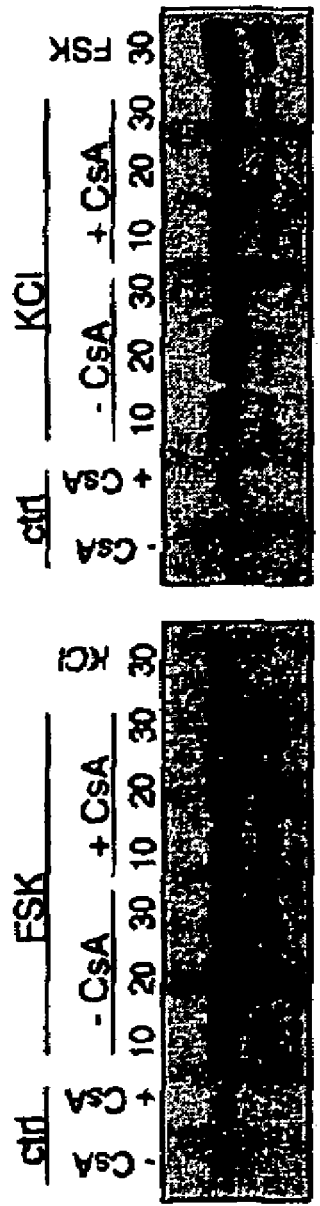
FIG. 9 illustrates the time course (in minutes) of CREB Ser133 phosphorylation in HIT cells following treatment with forskolin (10 µM) or KCl (45 mM). The effect of cyclosporine A (CsA: 5 µM) is shown. Immunoreactive bands correspond to phospho (Ser133) CREB (top) and phospho (Ser63) ATF1 (bottom).

The importance of Ser133 phosphorylation for CREB activation in response to cAMP and calcium signals (Shaywitz and Greenberg, 1999) prompted examination of the extent to which this site mediates cooperativity between both pathways. Treatment with forskolin and KC1 increased levels of CREB Ser133 phosphorylation in HIT cells (see FIGS. 1C and 9); but co-stimulation with forskolin plus KC1 had no additional effect on phospho (Ser 133) CREB levels relative to forskolin alone. Despite its ability to inhibit CREB activity in cells stimulated with cAMP and calcium agonists, CsA had no effect either on the stoichiometry or kinetics of CREB Ser133 phosphorylation in response to these signals (see FIGS. 1C and 9). These results suggest that calcium and cAMP act synergistically on a calcineurin regulated component which is distinct from the CREB Ser133 phospho-acceptor site.

The recruitment of CBP/P300 to the promoter is thought to be a common pathway for activation of cellular genes via CREB in response to various stimuli (Goodman and Smolik, 2000). To compare the effects of calcium and cAMP pathways in promoting the CREB:CBP interaction, mammalian two-hybrid assays were performed using GAL4-KID and KIX-VP 16 expression vectors. Addition of forskolin to HIT cells stimulated the KID:KIX interaction 20-fold by GAL4 luciferase reporter assay; but KC1 depolarization had no effect in this regard, despite its ability to induce comparable levels of Ser133 phosphorylation (see FIG. 1D). Addition of forskolin with KC1 rescued KID:KIX complex formation, albeit at similar levels to forskolin alone (see FIG. 1D). These results indicate that the cooperativity between calcium and cAMP signals on CREB target gene expression is not reflected at the level of the KID:KIX interaction.

Previous reports suggesting that the CREB bZIP domain contributes to target gene activation by CREB (Bonni et al., 1995a) prompted testing of the importance of this domain in mediating cooperativity between cAMP and calcium signals. In transient assays of HIT cells using a GAL4-CREB polypeptide containing the GAL4 DNA binding domain fused to CREB, KC1 and forskolin induced GAL4 reporter activity 2 and 5-fold individually but 22-fold when added in combination; and these stimulatory effects were potently inhibited by CsA (see FIG. 1E). By contrast, a truncated GAL4-CREBΔbZIP polypeptide lacking the C-terminal bZIP domain (aa. 284-341) in CREB showed only a modest response to forskolin and no induction by KC1. Notably, the GAL4-CREBΔbZIP polypeptide elicited no cooperativity between cAMP and calcium agonists, revealing the importance of the bZIP domain for this effect.

Example 2

TORCs Promote CREB Activation in Response to cAMP and Calcium Signals

Figure 2:
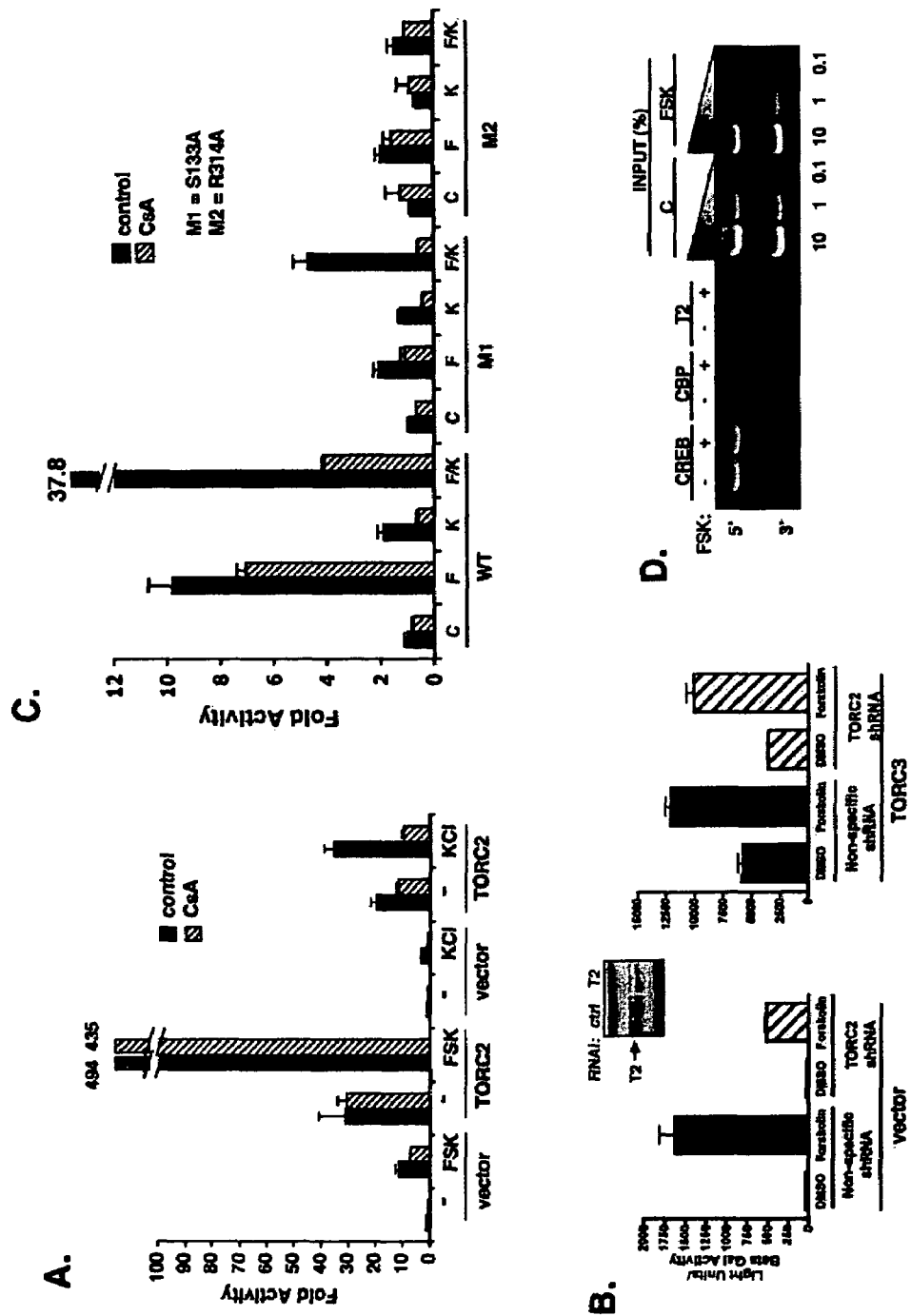
FIGS. 2A-2D demonstrate that TORC2 is recruited to the promoter and mediates CREB target gene activation in response to CAMP and calcium signals. Specifically, FIG. 2A summarizes the results of a transient assay of HIT cells co-transfected with CREB-dependent EVX-1 luciferase reporter and TORC2 expression vector, or control empty vector. Cells were treated with forskolin or KCl as indicated. The effect of CsA (5 μM) is shown.

The involvement of the CREB bZIP domain in mediating cooperativity between cAMP and calcium signals prompted examination of the role of TORCs, a family of CREB coactivators which bind directly to the bZIP, in this process. The TORC family comprises three members (TORC1, TORC2, TORC3) each of which contains highly conserved N-terminal CREB binding (aa. 1-42 in TORC1) and C-terminal trans-activation (aa. 517-634) domains (Conkright et al., 2003a; Iourgenko et al., 2003). Over-expression of TORC2 induced basal EVX-1 promoter activity 20-30 fold; and treatment with cAMP or calcium channel agonist further potentiated the reporter 25-fold and 30-fold, respectively, suggesting that TORC2 is regulated by both signals (see FIG. 2A). Consistent with the notion that TORC2 mediates CREB target gene expression via a calcineurin dependent mechanism, addition of CsA disrupted TORC2 activity in HIT cells treated with KC1 (see FIG. 2A).

To determine whether TORC2 is necessary for cAMP dependent induction of CREB target genes, knockdown experiments were performed in HEK293T cells for their high transfection efficiency relative to HIT cells. Consistent with its ability to potentiate CREB activity in response to cAMP and calcium agonists, TORC2 was observed to facilitate target gene activation; knockdown of TORC2 expression with a TORC2 RNAi construct reduced TORC2 protein levels and disrupted cAMP dependent induction of the EVX-1 promoter relative to a non-specific RNAi plasmid (Conkright et al., 2003a) (see FIG. 2B, left panel). Expression of TORC3, which is not recognized by the TORC2 RNAi construct, rescued induction of the EVX-1 promoter by cAMP agonist (see FIG. 2B, right panel).

To further evaluate the role of TORCs in CREB activation, a screen was conducted in efforts to identify TORC interaction-defective CREB polypeptides. Based on previous data showing that the CREB bZIP domain mediates complex formation with TORC (Conkright et al., 2003a), basic and leucine zipper regions were tested separately in pull down assays; it was determined that the leucine zipper motif alone was sufficient for binding to TORC.

Figure 10:
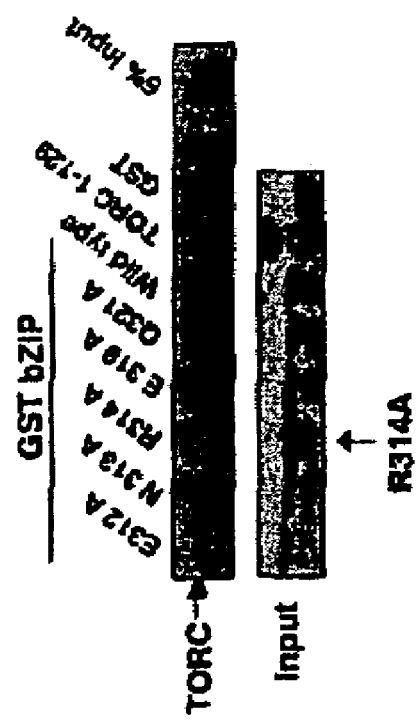
FIG. 10 presents the characterization of a TORC interaction defective mutant CREB polypeptide. A pull-down assay of $^{35}$S-labeled TORC1 was carried out with wild-type and mutant GST CREB hZIP (amino acid residues 284-341) polypeptides. The effect of alanine substitutions at polar residues in the leucine zipper domain on TORC binding are shown. Binding of TORC to itself via N-terminal coiled-coil domain (TORC1-129) is shown for comparison. Coomassie stained gel showing comparable input levels of GST-CREB bZIP proteins was used for the pull-down assays.
Figure 11:
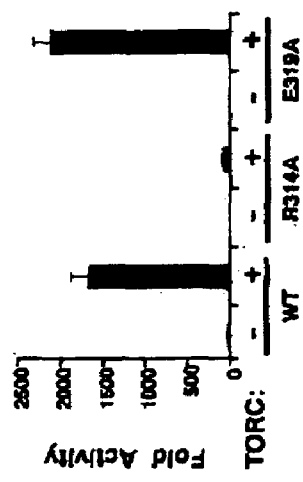
FIG. 11 presents the results of transient assays of HEK293T cells transfected with flag-tagged wild-type, Arg314Ala (R314A), and Glu319Ala (E319A) CREB plus TORC1 expression vector. Luciferase activity obtained from co-transfected EVX-1 reporter plasmid is shown. Comparable binding of wild-type and mutant Arg314Ala (R314A) CREB to the CRE was verified by gel mobility shift assay (not shown).

Mutagenesis studies on charged residues within the leucine zipper were then carried out due to the sensitivity of the CREB:TORC complex to high salt disruption. Out of five independent mutants tested, only one, Arg314A1a, showed substantially no TORC binding activity (see FIG. 10). Interestingly, Arg314 is conserved amongst CREB family members (CREB1, ATF1, CREM), consistent with the suggestion of a potential role for this residue in CREB dependent transcription. By contrast with its potent activity on wild-type CREB protein, TORC1 had no effect on the EVX-1 reporter in cells expressing the CREB Arg314Ala mutant, demonstrating the importance of this amino acid for CREB activation via TORC1 (see FIG. 11).

Figure 12:
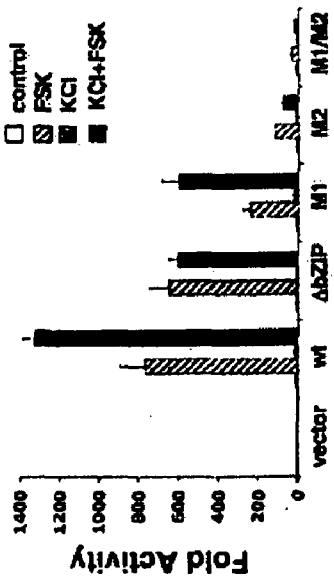
FIG. 12 indicates the relative importance of CREB:CBP and CREB:TORC complexes for transcriptional activation in response to CAMP and calcium signals in PC12 cells. Transient assay was conducted with PC12 cells co-transfected with wild-type, CBP interaction defective (M1: Ser133Ala), TORC interaction defective (M2: Arg314Ala), or CBP and TORC defective (M1/M2) GAL4-CREB expression vectors as indicated. The activity was determined for cotransfected GAL4 luciferase reporter in cells treated with forskolin (10 µM), KCl (45 mM), or forskolin plus KCl for four hours as shown.

To compare the relative contributions of CREB:CBP and CREB:TORC complexes for cellular gene induction, transient assays of HIT cells were performed with GAL4-CREB polypeptides containing point mutations that disrupt interactions with CBP (M1: Ser133Ala), or TORC (M2: Arg314Ala). By contrast with the wild-type GAL4-CREB polypeptide, the CBP interaction defective M1 mutant was less responsive to cAMP (10-fold vs. 2.5 fold), but remained sensitive to cooperative effects of cAMP and KCl as well as to the inhibitory effects of CsA (see FIG. 2C). Mutagenesis of Arg314 in GAL4-CREB (M2) not only disrupted cAMP inducibility, but also compromised cooperativity between cAMP and KCl (see FIG. 2C). Similar results were noted in other electrically excitable cells including PC12 pheochromocytoma cells (see FIG. 12), consistent with the hypothesis that TORCs function in a variety of cellular contexts.

The apparent requirement of CBP and TORC complexes for cellular gene activation via CREB prompted examination of whether these proteins are recruited to the promoter by chromatin immunoprecipitation (ChIP) assay. This analysis was conducted in HEK293T cells due to the absence of hamster genomic sequence data for CREB target genes. In ChIP assays on the endogenous CREB target gene NR4A2 (Conkright et al., 2003b), it was found that CREB occupied the promoter both under basal conditions and in response to cAMP treatment (see FIG. 2D). CBP and TORC2 were absent from the NR4A2 promoter under basal conditions; following treatment with forskolin for 30 minutes, both were recruited to the promoter but not to a control 3' end fragment of the NR4A2 gene. These results are consistent with functional data from both TORC2 knockdown and CREB mutagenesis assays (see FIGS. 2B and 2C) demonstrating the role of TORC2 as a signal-dependent CREB coactivator.

Example 3

TORCs Migrate to the Nucleus in Response to cAMP

Figure 13:
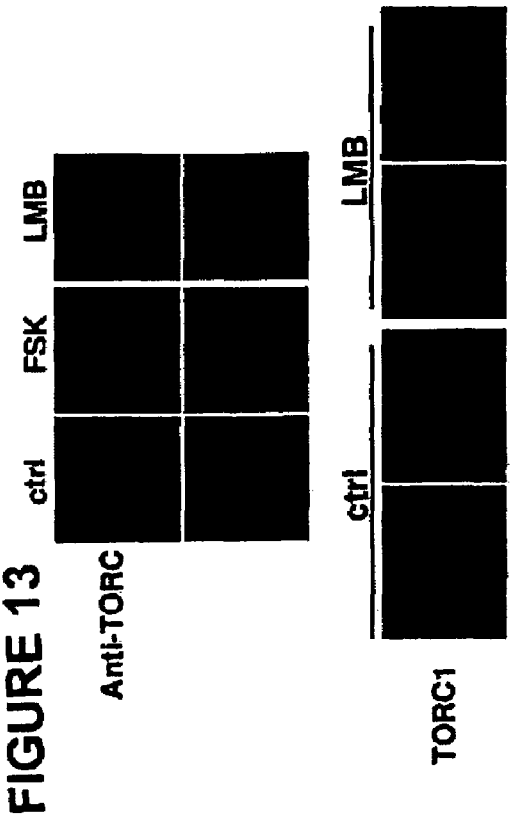
FIG. 13, top panels, illustrates the cellular localization of endogenous TORC proteins in ATYBI cells using TORC specific antiserum. The effect of forskolin (10 µM, 30 minutes) and leptomycin B (LMB, 10 ng/ml, 2 hr) treatment is shown. DAP1 staining is shown below to visualize the nuclei.

Immunofluorescence studies were performed to determine the mechanism by which cAMP triggers recruitment of TORC2 to the promoter. The relative absence of cytoplasm in HIT cells for microscopic analysis of TORC localization prompted the use of human ATYB1 fibroblasts. Flag-tagged and endogenous TORC2 proteins were largely confined to the cytoplasm of ATYB1 cells under basal conditions; and treatment with cAMP agonist promoted nuclear accumulation of TORC2 within 30 minutes (see FIGS. 3A and 13). Treatment with the exportin inhibitor leptomycin B (LMB) strongly enhanced nuclear accumulation of both endogenous and transfected TORC1 and TORC2 within 30 to 60 minutes, indicating that these proteins likely cycle in and out of the nucleus in the absence of cellular stimulus (see FIGS. 3B and 13).

Figure 14:
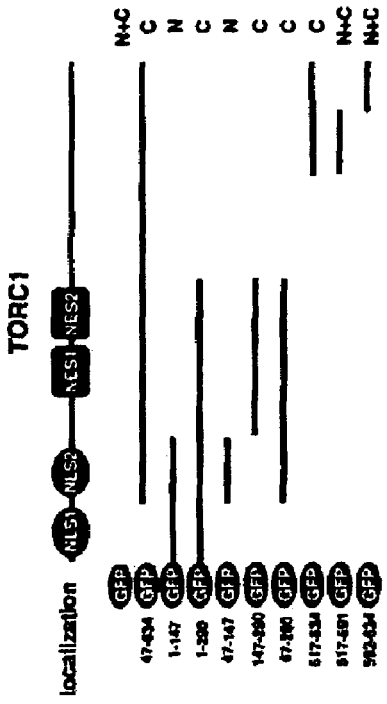
FIG. 14 identifies nuclear localization (NLS) and nuclear export (NES) signals in TORC. Summary in the right margin thereof shows the predominant cellular location (Nuclear:N, Cytoplasmic:C) of TORC2 polypeptides fused to green fluorescent protein (GFP). TORC2 amino acid endpoints for each fusion protein shown.

To characterize regions in TORC that promote either cytoplasmic or nuclear accumulation, cellular fluorescence assays were performed on truncated TORC1 polypeptides fused to green fluorescent protein (GFP). Nuclear localizing activities (NLS1 and NLS2) were detected near the N-terminus of TORC1 (aa. 1-147), whereas nuclear export sequences (NES1, NES2) were located within the central Ser/Pro rich domain from aa. 148-290 (see FIG. 14). Both NLS and NES motifs were well conserved within the three TORC family members, and mutagenesis of individual leucines in NES1 and NES2 promoted nuclear accumulation of TORCs.

Figure 3:
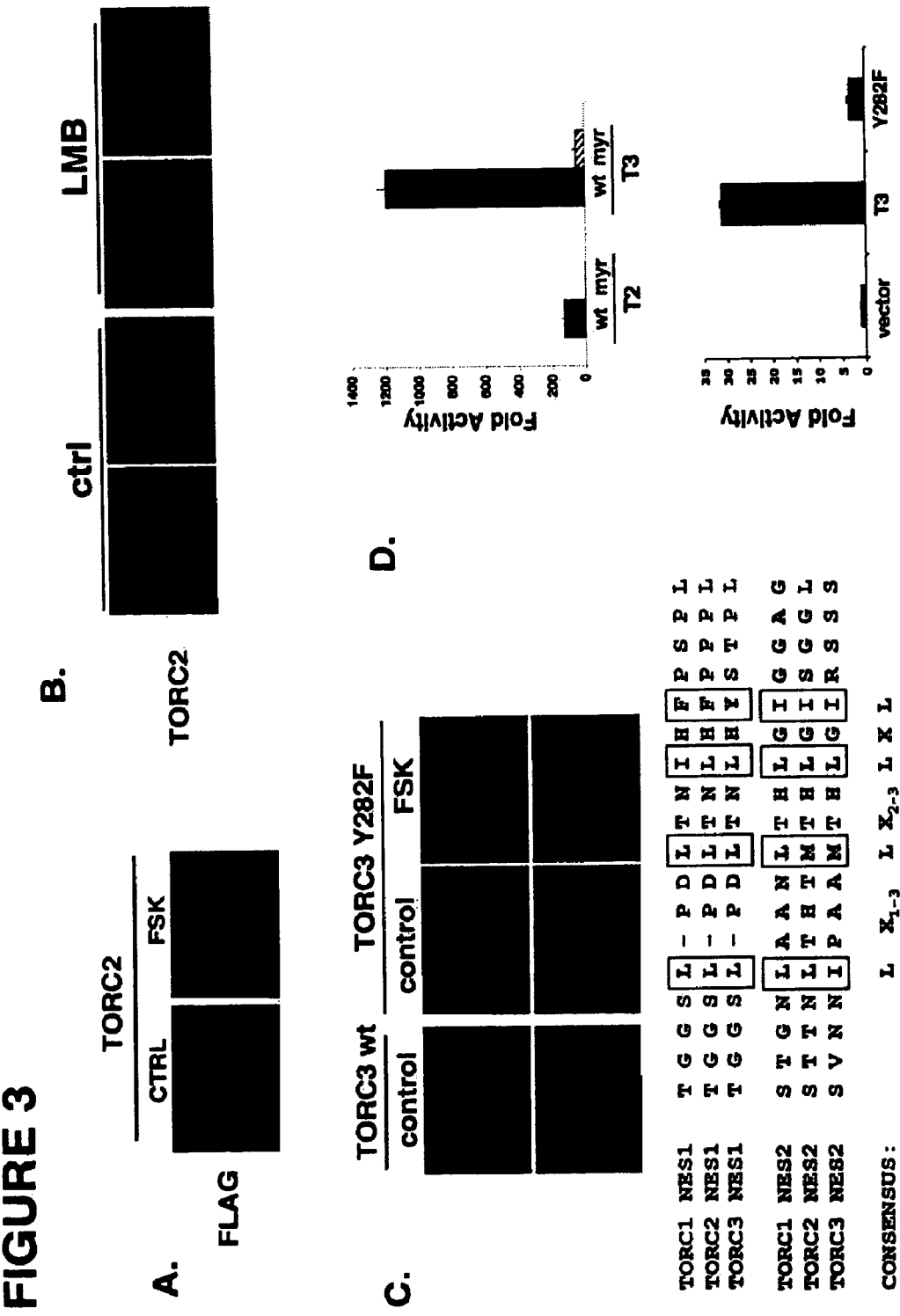
FIGS. 3A-3D demonstrate that cAMP promotes cytoplasmic to nuclear translocation of TORC2. Specifically.

TORC3 contains a Phe to Tyr282 substitution in NES1, which would be predicted to disrupt export activity (see FIG. 3C, bottom). Indeed, TORC3 was localized exclusively in the nucleus of both control and cAMP stimulated cells (see FIG. 3C, top); consistent with its nuclear location, wild-type TORC3 was far more active in potentiating CREB activity under basal conditions relative to TORC2 (see FIG. 3D). Conversely, addition of an N-terminal src myristylation signal targeted TORC3 to the cytoplasm and rendered the protein transcriptionally inactive (see FIG. 3D). Likewise, mutagenesis of Tyr282 in TORC3 to Phe promoted cytoplasmic accumulation of the protein and repressed basal TORC3 activity. cAMP treatment triggered translocation of mutant TORC3 Tyr282Phe to the nucleus, consistent with the notion that cAMP stimulates nuclear entry of TORC proteins (see FIG. 3C).

Example 4

TORC is Dephosphorylated in Response to cAMP and Calcium Signals

Figure 4:
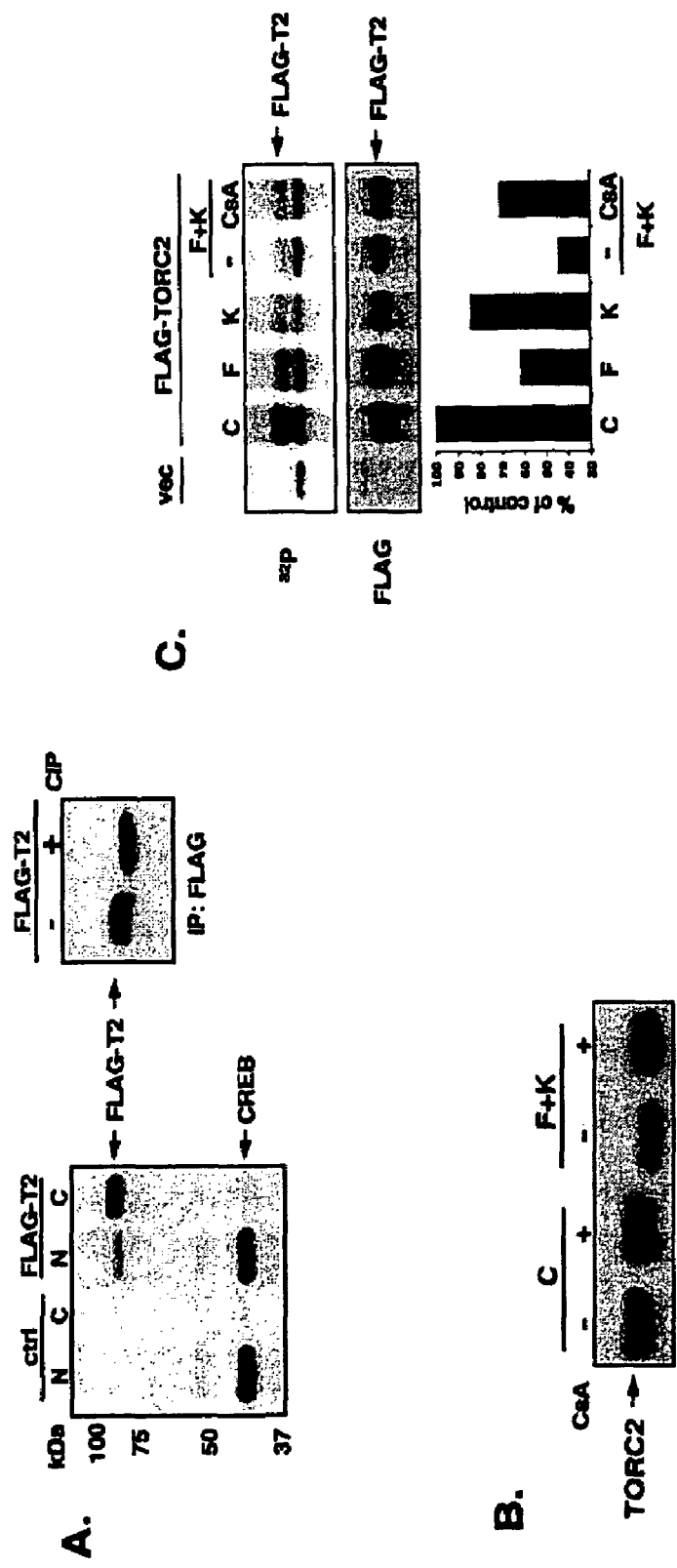
FIGS. 4A-4C demonstrate that cAMP and calcium promote TORC2 dephosphorylation and nuclear entry. Specifically, FIG. 4A, left panel, presents a Western blot of nuclear (N) and cytoplasmic (C) fractions from HEK293T cells transfected with Flag-tagged TORC2 (FLAG-T2) or empty vector (ctrl). Compare the mobility of TORC2 immunoreactive bands. Endogenous CREB immunoreactivity is shown to verify the efficient fractionation of cytoplasmic and nuclear extracts.

To determine the mechanism by which extracellular signals regulate TORC2 nuclear entry, the biochemical properties of TORC2 were compared in nuclear and cytoplasmic fractions of HEK293T cells. Flag-tagged TORC2 appeared as an 85 kD doublet in cytoplasmic fractions and as a single faster migrating species in nuclear extracts (see FIG. 4A, left panel). Indeed, treatment with calf intestinal alkaline phosphatase (CIP) transformed the cytoplasmic TORC2 doublet into a single faster migrating species, consistent with the belief that TORC2 undergoes dephosphorylation upon nuclear entry (see FIG. 4A, right panel).

To determine whether TORC2 phosphorylation is regulated in response to calcium and cAMP signals, Western blot assays were performed on endogenous TORC2 protein in HIT cells. Consistent with results using the Flag-tagged protein, endogenous TORC2 also appeared as two closely migrating bands in total extracts (see FIG. 4B). Co-stimulation with KCl plus forskolin promoted extensive TORC2 dephosphorylation; and pre-treatment with CsA partially reversed this effect, consistent with the belief that calcineurin promotes TORC2 dephosphorylation in response to these inducers (see FIG. 4B).

To evaluate the status of TORC2 phosphorylation directly, $^{32}$P-labeling experiments were performed. SDS-PAGE analysis of flag-tagged TORC2 immunoprecipitates from HIT cells revealed that in vivo $^{32}$P-labeled TORC2 was dephosphorylated within 10 minutes after treatment with forskolin or KCl (see FIG. 4C). Co-stimulation with forskolin and KCl reduced phospho-TORC2 levels further; these effects were blocked by co-treatment with CsA, consistent with the belief that calcineurin promotes TORC2 dephosphorylation in this setting (see FIG. 4C). TORC2 appears to be phosphorylated exclusively on serine by phospho-amino acid analysis; and two dimensional tryptic mapping of $^{32}$P-labeled TORC2 reveals at least seven spots of comparable intensity, indicating that TORC2 is extensively phosphorylated at numerous sites.

Example 5

TORCs Associate with 14-3-3 Proteins

To clarify the mechanism by which TORC phosphorylation promotes its cytoplasmic retention, proteomic analyses were performed to search for TORC interacting proteins. Immunoprecipitates of TORC1 and TORC2 were prepared from stable cell lines expressing Flag-tagged versions of either protein. Both TORCs were found to interact strongly with multiple members of the 14-3-3 family of proteins (e.g., 92.5% coverage for 14-3-3E). 14-3-3 proteins have been found to bind a number of regulatory proteins, most notably CDC25A, forkhead, and NFAT family members, and to inhibit their biological function (Brunet et al., 1999; Chen et al., 2003; Chow and Davis, 2000; Durocher et al., 2000).

Figure 5:
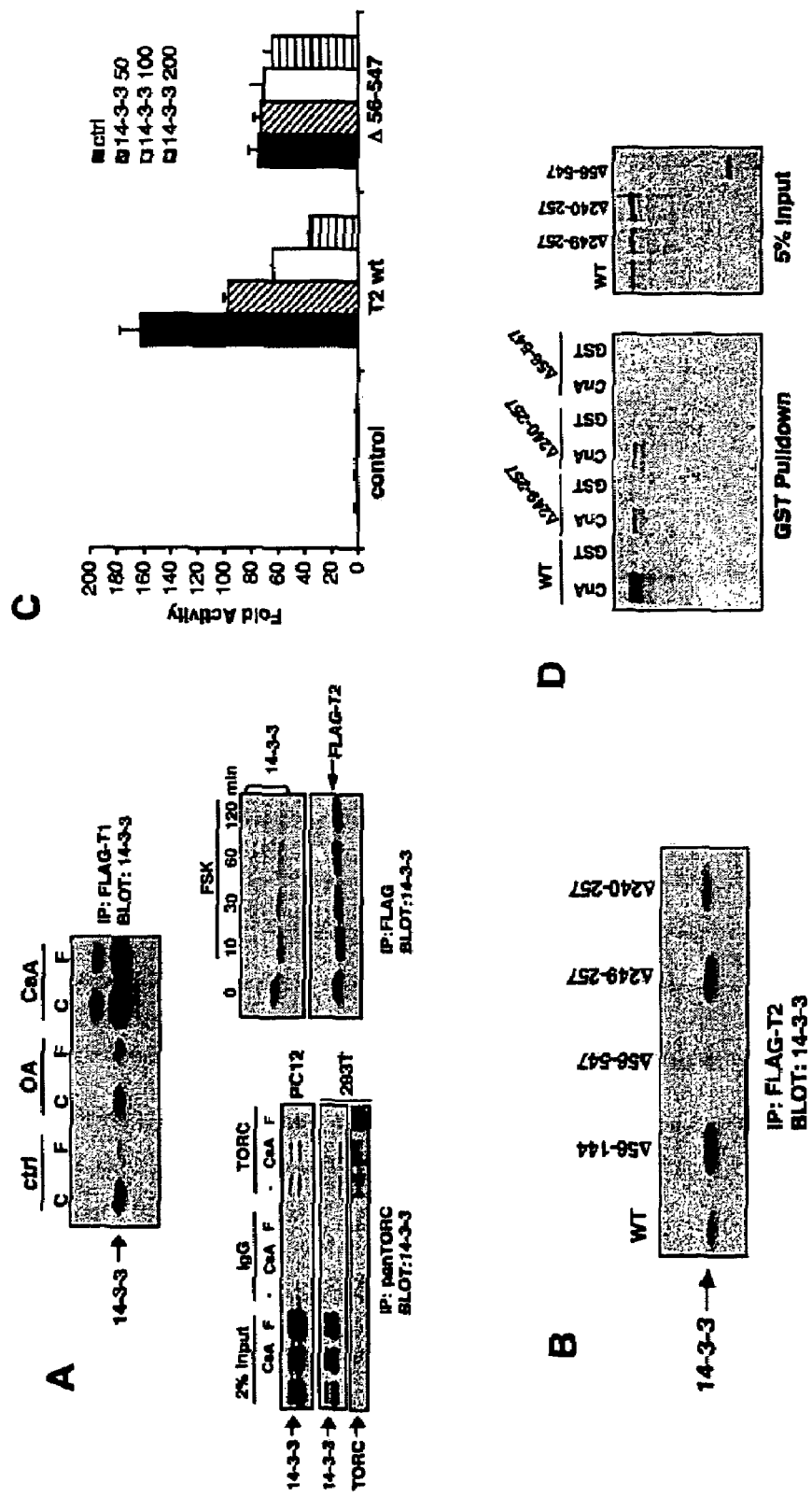
FIGS. 5A-5D illustrate that 14-3-3 proteins associate with and repress TORC activity. Specifically, FIG. 5A, top panel, presents the results of a coimmunoprecipitation assay of Flag-TORC1 with endogenous 14-3-3 proteins in HEK293T cells. The effect of forskolin (F) treatment on the TORC 1:14-3-3 association is shown. The relative effect of Ser/Thr phosphatase PP1/PP2A (okadaic acid; OA) or CsA on TORC1: 14-3-3 interaction is indicated.

Co-immunoprecipitation studies were performed to confirm the proteomic results and to explore the potential role of 14-3-3 proteins in regulating TORC activity. Endogenous 14-3-3 proteins were recovered from immunoprecipitates of Flag-TORC1 and Flag-TORC2 expressing cells as well as from immunoprecipitates of endogenous TORC proteins from HEK293T and PC12 cells (see FIG. 5A). Consistent with its ability to promote TORC translocation to the nucleus, forskolin treatment disrupted both transfected Flag-TORC 1:14-3-3 (see FIG. 5A, top panel) and endogenous TORC: 14-3-3 interactions (see FIG. 5A, bottom left panel). The kinetics of TORC2: 14-3-3 dissociation parallel the time course for TORC2 dephosphorylation and nuclear entry in response to cAMP agonist; in co-immunoprecipitation studies of Flag-TORC2 and 14-3-3 proteins, the TORC2:14-3-3 interaction was diminished by about half within 10 minutes of forskolin treatment and was maximally reduced after 30 to 60 minutes (see FIG. 5A, bottom right panel).

The general importance of Ser/Thr phosphorylation for association with 14-3-3 family members prompted examination of whether the inhibitory effects of CsA on TORC activity correlate with changes in TORC: 14-3-3 binding. CsA treatment greatly enhanced complex formation under basal and cAMP stimulated conditions, whereas the protein phosphatase PP1/PP2A inhibitor okadaic acid (OA) had no effect on this interaction. These data are consistent with the belief that calcineurin mediates dissociation of TORC: 14-3-3 complexes in response to calcium signals by dephosphorylation of TORCs (see FIG. 5A).

Co-immunoprecipitation studies were performed on mutant TORC polypeptides to identify regions in TORC2 that mediate the 14-3-3 interaction. The central Ser/Pro rich domain in TORC2 (aa. 56-547) appeared important in this regard; relative to other mutant TORC2 polypeptides, no endogenous 14-3-3 proteins were recovered from immunoprecipitates of mutant TORC2 (A56-547) (see FIG. 5B). Consistent with its proposed role in promoting cytoplasmic retention of TORC proteins, over-expressed 14-3-3 beta inhibited basal EVX-1 reporter activity in HEK293T cells transfected with a TORC2 expression vector. By contrast, 14-3-3 beta over-expression had no effect on the activity of the TORC2 (A56-547) protein, demonstrating the importance of the TORC: 14-3-3 interaction for repression of CREB target genes (see FIG. 5C).

The ability of CsA to block TORC2 dephosphorylation and to enhance the 14-3-3 interaction prompted an evaluation of the role of calcineurin in this process. Remarkably, calcineurin A and B subunits were identified in proteomic analyses of Flag-tagged TORC1 (10.4% peptide coverage) and TORC2 (7.9% peptide coverage) immunoprecipitates. TORC2 appears to bind to calcineurin A directly; in pull-down assays $^{35}$S-labeled TORC2 was efficiently precipitated with GST-calcineurin A (aa. 1-347) but not GST beads (see FIG. 5D, bottom panel). The 14-3-3 interaction-defective TORC2 (Δ56-547) protein, lacking the central regulatory domain, was also unable to associate with calcineurin, demonstrating the importance of this region in TORC2 for signal dependent modulation.

Example 6

TORC2 Associates with SIK2, a snf1 Related Kinase

The high levels of cytoplasmic TORC2 phosphorylation on serine under basal conditions prompted testing to determine whether TORCs associate with a Ser/Thr kinase activity. Both endogenous and over-expressed TORC2 were readily phosphorylated by in vitro kinase assay of immunoprecipitates prepared from cytoplasmic (C) but not from nuclear (N) fractions of HEK293T cells (see FIG. 6A). TORC associated kinase activity was potently inhibited by treatment with forskolin (compare intensities of 85kD TORC2 bands), consistent with one of two explanations, i.e., that PKA either reduces the activity of the kinase or disrupts the TORC2: kinase complex. Two dimensional phospho-tryptic mapping studies of $^{32}$P-labeled flag-tagged TORC2 revealed a single major spot following in vitro kinase assay of TORC2 immunoprecipitates, consistent with the explanation that TORC associated kinase phosphorylates TORC2 at one principal site rather than at the multiple sites observed in vivo.

Figure 6:
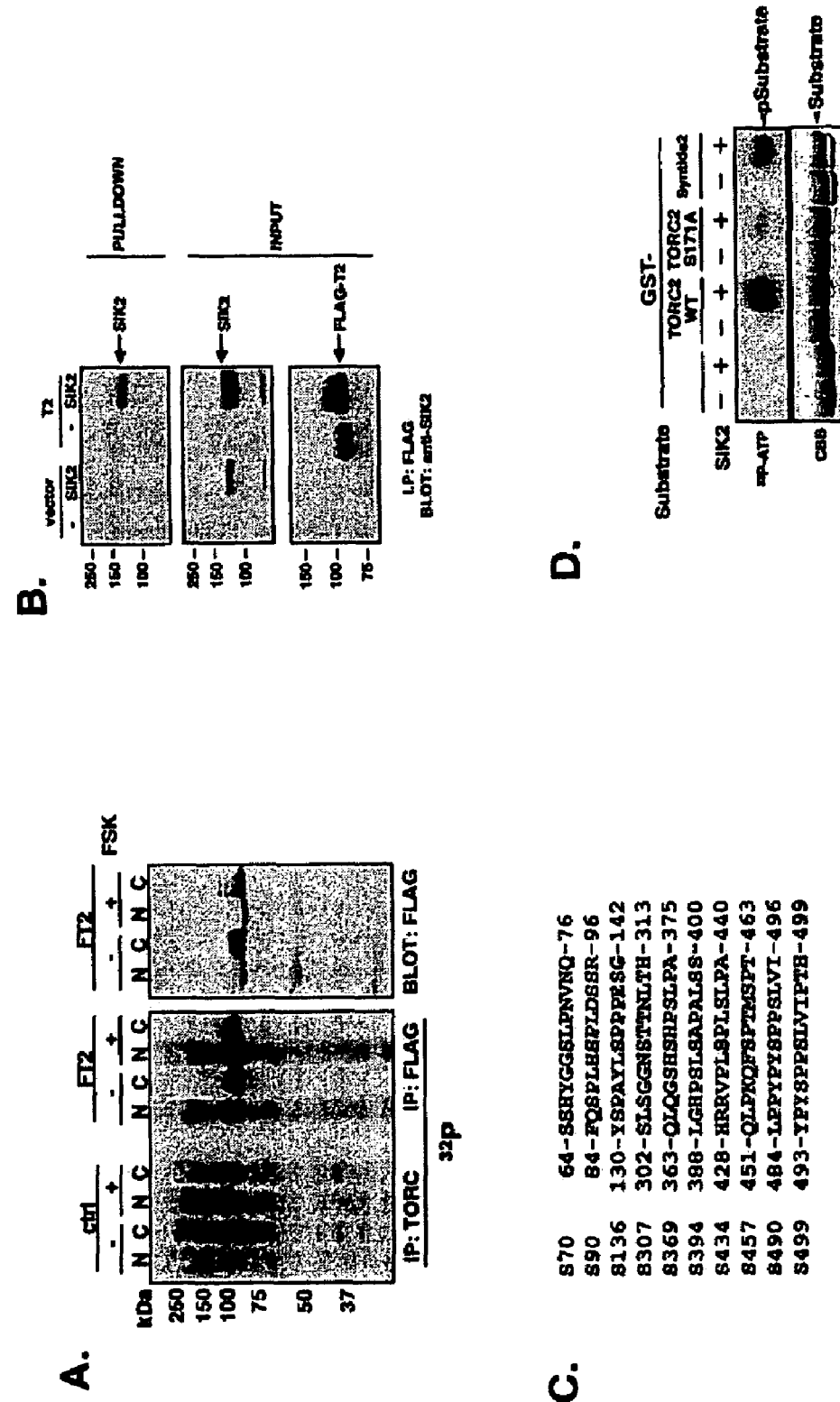
FIGS. 6A-6D demonstrate that SIK2 (or related family members), snf1-like kinase, associates with and phosphorylates TORC2. Specifically, FIG. 6A demonstrates that TORCs associate with a cytoplasmic protein kinase activity. In vitro kinase assays of endogenous TORC (1P:TORC) and transfected Flag-tagged TORC2 (1P:FLAG) immunoprecipitates were prepared from nuclear or cytoplasmic fractions of control and forskolin treated cells as shown. $^{32}$P-labeled bands (left) and corresponding protein levels by Western blot assay (right) are indicated.

Proteomic analysis of Flag-TORC2 immunoprecipitates prepared from transfected HEK293T cells revealed the presence of the Salt Inducible Kinase 2 (SIK2: 6 peptides, 11.7% coverage), a member of the snf1 family of energy-sensing kinases previously found to inhibit transcription of cAMP responsive genes (Doi et al., 2002). Confirming this finding, SIK2 was readily detected in anti-flag immunoprecipitates prepared from 11 EK293T cells co-transfected with SIK2 and Flag-tagged TORC2 expression vectors (see FIG. 6B). Moreover, TORC2 mobility was noticeably reduced in cells co-expressing SIK2, consistent with the suggestion that this kinase directly phosphorylates TORC2 (see FIG. 6B, compare lanes 3,4).

To identify sites on TORC2 that are phosphorylated by SIK2 and other cellular kinases, tandem mass spectroscopic (MS/MS) analysis was performed of TORC2 phospho-peptides generated from TORC2 immunoprecipitates. Eleven phospho-peptides were recovered by this analysis; and most of these mapped to the central regulatory domain (see FIG. 6C). Remarkably, one TORC2 phospho-peptide corresponded to an optimal site for SIK2 phosphorylation (LXB (S/T)XSXXXL (SEQ ID NO:7): aa.166-LNRTSSDSAL (SEQ ID NO:8) in TORC2 (see FIG. 15)). To determine whether Ser171 in TORC2 is indeed phosphorylated by SIK2 in vitro kinase assays were performed using a GST-TORC2 (aa 161-181) substrate. In $^{32}$P-labeling studies, SIK2 was found to phosphorylate wild-type but not Ser171 Ala mutant TORC2 in vitro, consistent with the suggestion that SIK2 phosphorylates TORC2 at a single site under basal conditions (see FIG. 6D).

Example 7

Figure 7:
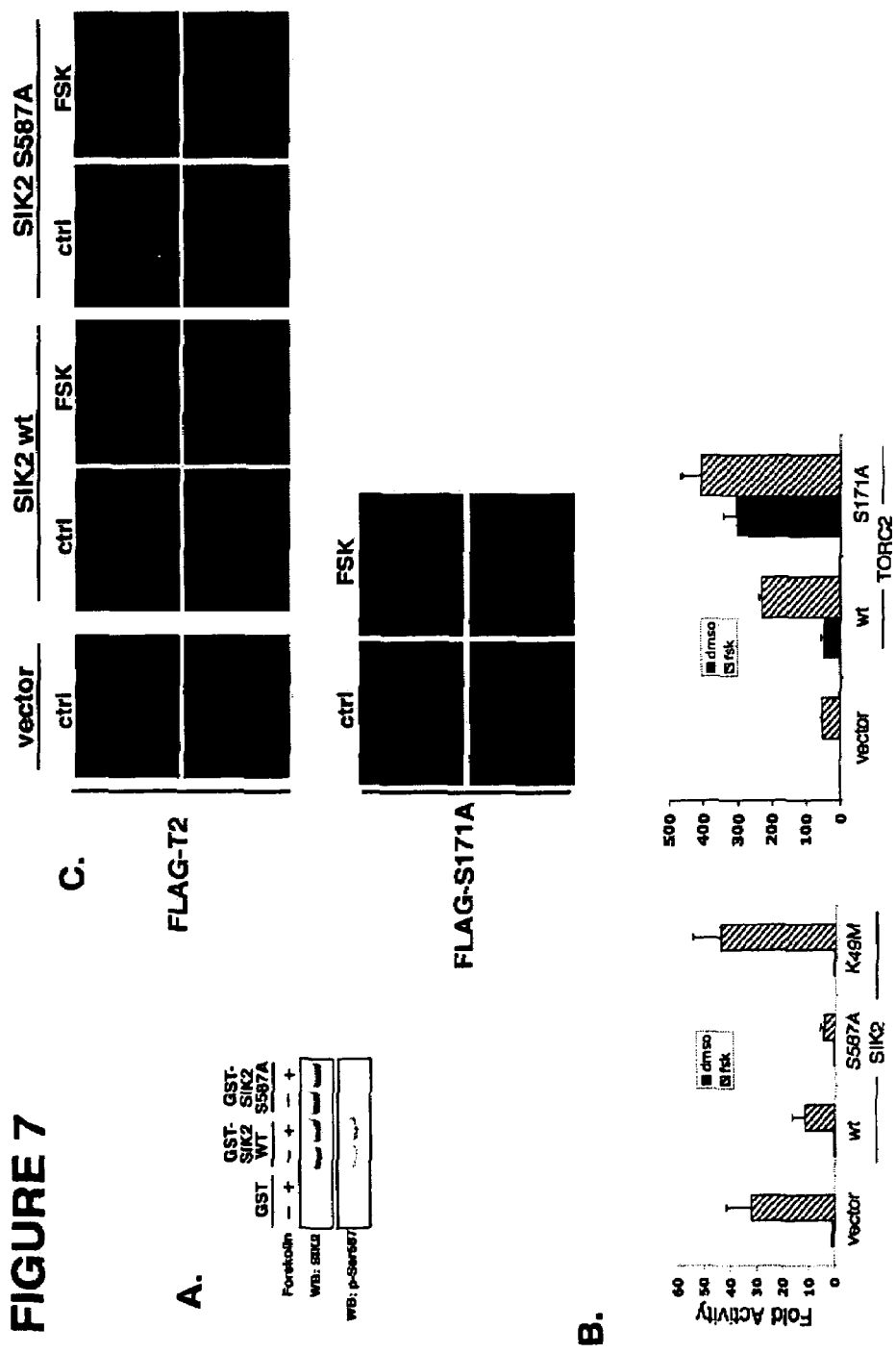
FIGS. 7A-7C demonstrate that TORC2 is retained in the cytoplasm under basal conditions via SIK2 (or related family members)-dependent phosphorylation at Ser171. Specifically.

SIK2 Inhibits TORC2 Nuclear Translocation cAMP has been reported to disrupt the inhibitory effects of SIK2 on CREB activity via the PKA mediated phosphorylation of SIK2 at Ser587 (Okamoto et al., 2004). Indeed, treatment with cAMP agonist induced phosphorylation of SIK2 at Ser587, by Western blot assay of GST-SIK2 expressing cells with phospho-Ser(587) specific antiserum (see FIG. 7A). Consistent with its proposed role in regulating CREB activity, endogenous SIK2 was readily detected in HIT cell extracts by Western blot assay. To further explore the functional role of SIK2 in modulating CREB-dependent gene expression, transient assays were performed on HEK293T cells co-transfected with the EVX-1 reporter plasmid. Over-expression of wild-type SIK2 blocked reporter activity about 70% in cAMP stimulated cells; but kinase dead SIK2 (K49M) had no effect in this regard, demonstrating the importance of SIK2 catalytic activity for CREB inhibition (see FIG. 7B, left panel). PKA phosphorylation defective SIK2 (Ser587Ala) was far more potent in reducing CRE reporter activity, consistent with the belief that cAMP normally disrupts SIK2 activity in this context (see FIG. 7B, left panel).

To evaluate the effect of Ser171 phosphorylation by SIK2 on TORC2 activity, transient assays were performed on a Ser171Ala mutant TORC2 expression vector. Relative to the wild-type protein, TORC2 (Ser171Ala) was far more active in potentiating CREB activity under basal conditions, but displayed comparable activity to wild-type TORC2 following forskolin treatment (see FIG. 7B, right panel). These results are consistent with the suggestion that SIK2 dependent phosphorylation at Ser171 represses TORC2 under basal conditions; and that cAMP stimulates TORC2 activity by disrupting SIK2 mediated Ser171 phosphorylation.

The importance of TORC2 nuclear entry for target gene activation in response to cAMP prompted examination of the effect of SIK2 on TORC2 localization. Under basal conditions, flag-tagged TORC2 was localized to both nuclear and cytoplasmic compartments of ATYB 1 cells (see FIG. 7C). Over-expression of SIK2 efficiently blocked nuclear entry of TORC2 under basal conditions; and treatment with forskolin promoted nuclear entry of TORC2 in these cells, demonstrating the ability of PKA to overcome the inhibitory effects of SIK2 on TORC2 translocation. By contrast, TORC2 remained cytoplasmic even following cAMP treatment in cells expressing the PKA phosphorylation defective SIK2 (Ser587Ala), reinforcing the role of Ser587 for TORC2 activation. Phosphorylation of Ser171 by SIK2 appears important for cytoplasmic retention; mutant TORC2 (Ser171Ala) was targeted to the nucleus constitutively under both basal and cAMP stimulated conditions (see FIG. 7C). Taken together, these results are consistent with the proposal that the SIK2 mediated phosphorylation of TORC2 at a single site (Ser171) favors cytoplasmic retention of TORC2 and inhibition of CREB activity under basal conditions.

Example 8

TORC2, a Master Switch for Hepatic Gluconeogenesis

Under fasting conditions, pancreatic glucagon triggers the activation of catabolic programs in liver in part via the cAMP responsive factor CREB (see Herzig et al., 2001; Hall & Granner, 1999; and Hanson & Reshef, 1997). CREB in turn stimulates gluconeogenesis and fatty acid oxidation genes by inducing expression of the nuclear hormone receptor coactivator PGC-It (see Herzig et al., 2001 and Voon et al., 2001). Consistent with the above, mice deficient in PGC-1α display defects in hepatic gluconeogenesis and fatty acid oxidation (see Koo et al., 2004 and Lin et al., 2004).

Figure 16:
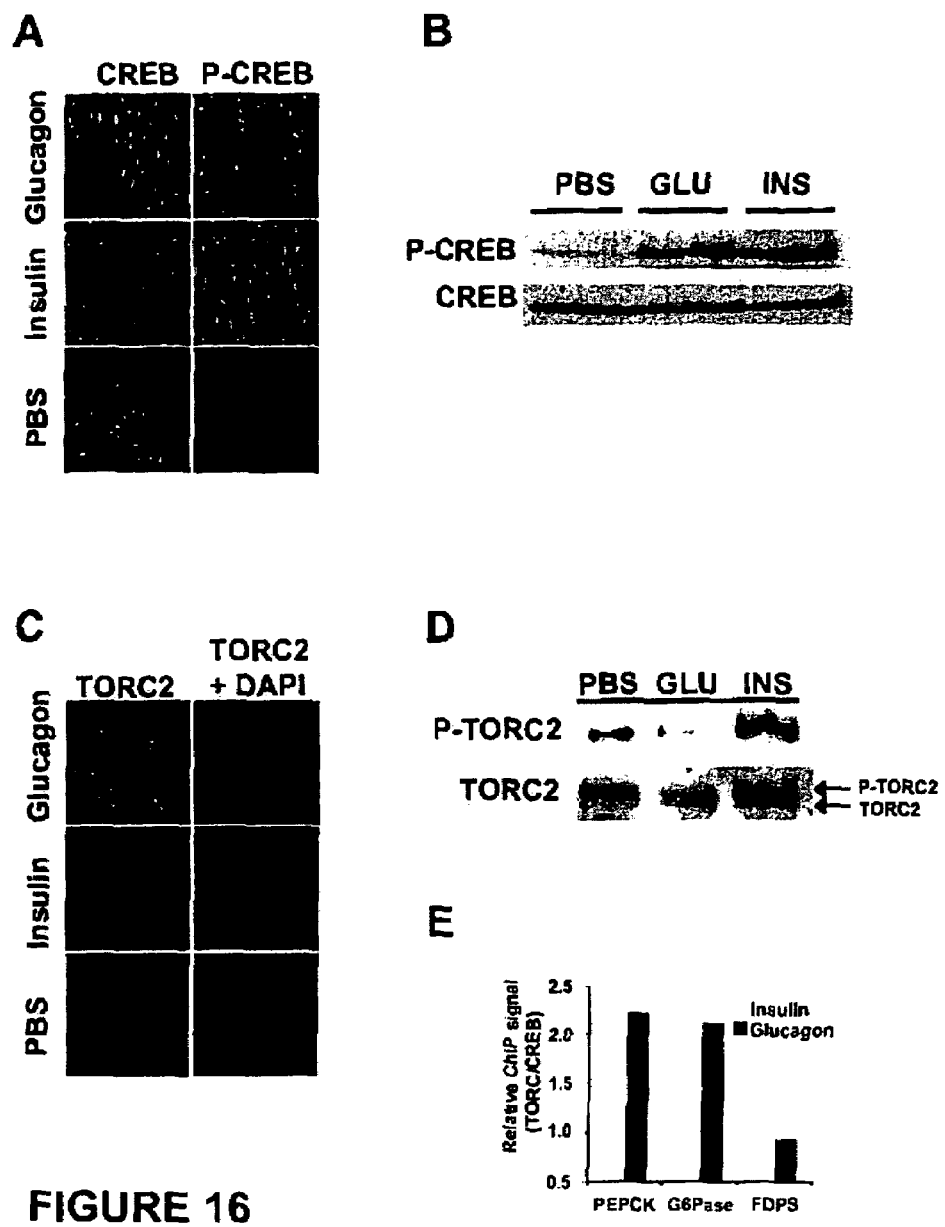
FIGS. 16A-16E illustrate the effect of fasting and feeding signals on activation of CREB:TORC and CREB:CBP pathways in liver. Specifically.

Glucagon is thought to enhance CREB activity via the PKA mediated phosphorylation of CREB at Ser133, and this modification in turn stimulates target gene expression via the recruitment of the coactivator CBP to the promoter (see Chrivia et al., 1993 and Arias et al., 1994). Intraperitoneal (IP) administration of glucagon was found to promote CREB Ser133 phosphorylation in liver within 10 minutes by histochemical and Western blot analysis (see FIGS. 16A and 16B). Unexpectedly, IP insulin administration had comparable effects on Ser133 phosphorylation in the liver, arguing against a pivotal role for the CREB:CBP pathway in discriminating between fasting and feeding signals (see FIGS. 16A and 16B).

In addition to promoting CREB phosphorylation, cAMP has also been found to stimulate cellular gene expression via the dephosphorylation and nuclear entry of TORCs, a family of cytoplasmic coactivators that enhances cellular gene expression via an interaction with the CREB basic region/leucine zipper (bZIP) DNA binding domain (see Conkright et al., 2003a and Iourgenko et al., 2003). Thus, TORC2 activity was examined, as this family member was expressed at highest levels relative to TORC1 and TORC3 in liver as determined by quantitative PCR analysis. Hepatic TORC2 was localized primarily in the cytoplasm under ad libitum feeding conditions by immuno-histochemical analysis of liver sections (see FIG. 16C). IP glucagon administration induced translocation of TORC2 to liver nuclei within 10 minutes. Despite its ability to promote CREB Ser133 phosphorylation, insulin did not stimulate nuclear entry of TORC2, demonstrating the capacity of this coactivator to discriminate between fasting and feeding signals. Consistent with these dynamics, TORC2 was highly phosphorylated at Ser171 under ad libitum or insulin stimulated conditions, but was dephosphorylated following glucagon induction (see FIG. 16D). Moreover, in chromatin immunoprecipitation (ChIP) assays of liver tissue, glucagons, but not insulin, promoted recruitment of TORC2 to gluconeogenic genes (see FIG. 16E). Taken together, these results demonstrate that, by contrast with CREB Ser 133 phosphorylation, TORC2 activity is selectively induced in response to fasting signals.

Figure 17:
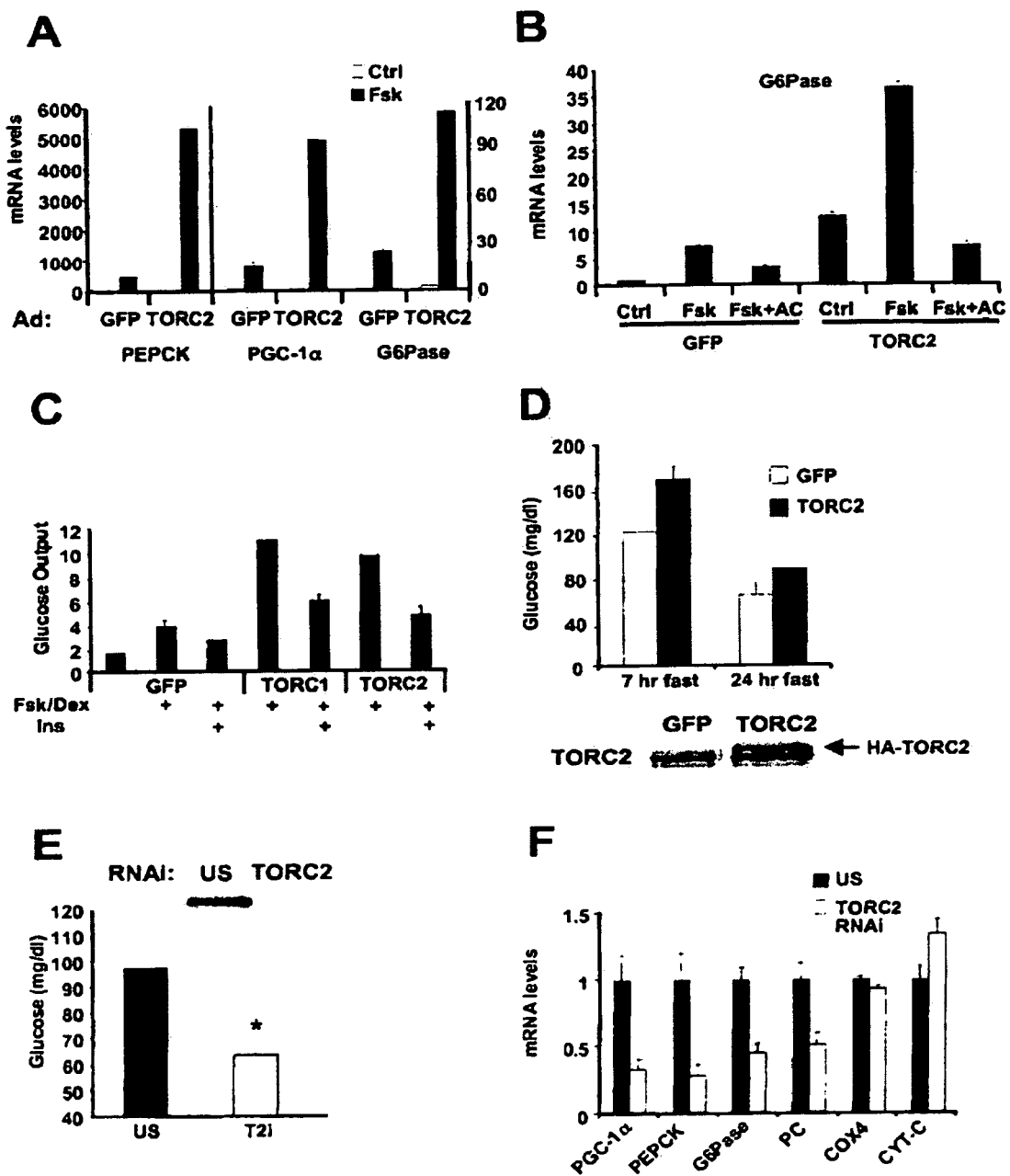
FIGS. 17A-17F demonstrate that TORC2 is required for hepatic gluconeogenesis during fasting. Specifically.

Based on its ability to translocate to the nucleus in response to glucagon, TORC2 would be expected to enhance gluconeogenic gene expression in a cAMP regulated manner. This proposal was tested by infecting primary rat hepatocytes with a TORC2 expressing adenovirus (Ad-TORC2). Ad-TORC2 had marginal effects on gluconeogenic genes (PGC-1α, PEPCK, and glucose 6 phosphatase) under basal conditions but potentiated the entire program 10-fold following exposure to Forskolin (FSK) (see FIG. 17A). The effects of Ad-TORC2 on gluconeogenic gene expression were CREB dependent; expression of a dominant negative A-CREB polypeptide, which specifically inhibits binding of CREB but not other bZIP family members to DNA (see Ahn et al., 1998), disrupted Ad-TORC2 potentiation (see FIG. 17B).

The ability of TORC2 to modulate gluconeogenic gene expression in hepatocytes exposed to cAMP agonist is consistent with the proposal that this coactivator modulates glucose output from the liver in response to fasting signals. Expression of either Ad-TORC2 or its paralog TORC1 in primary rat hepatocytes enhanced glucose output nearly 5-fold in cells exposed to FSK plus dexamethasone (see FIG. 17C); and glucose output from TORC over-expressing cells was disrupted by insulin treatment, demonstrating the ability of this coactivator to respond appropriately to both fasting and feeding signals. When expressed at levels comparable to the endogenous protein in liver, Ad-TORC2 promoted fasting hyperglycemia (see FIG. 17D). Levels of circulating insulin were elevated commensurately in Ad-TORC2 mice, indicating that the effects of this coactivator on hepatic glucose output are sufficient to trigger a counter-regulatory response.

Based on its ability to stimulate the gluconeogenic program and to promote hyperglycemia when over-expressed in mice, endogenous TORC2 is expected to regulate the response to fasting signals in liver. This expectation was tested employing a TORC2 RNAi construct that reduced expression of TORC2 proteins nearly 80% by Western blot assay (see FIG. 17E). Mice made acutely deficient in TORC2 by injection with the TORC2 RNAi adenovirus exhibited fasting hypoglycemia (60 mg/dl vs 100 mg/dl; see FIG. 17E); and mRNAs for gluconeogenic genes were reduced 3-fold on average relative to control littermates (see FIG. 17F).

Figure 18:
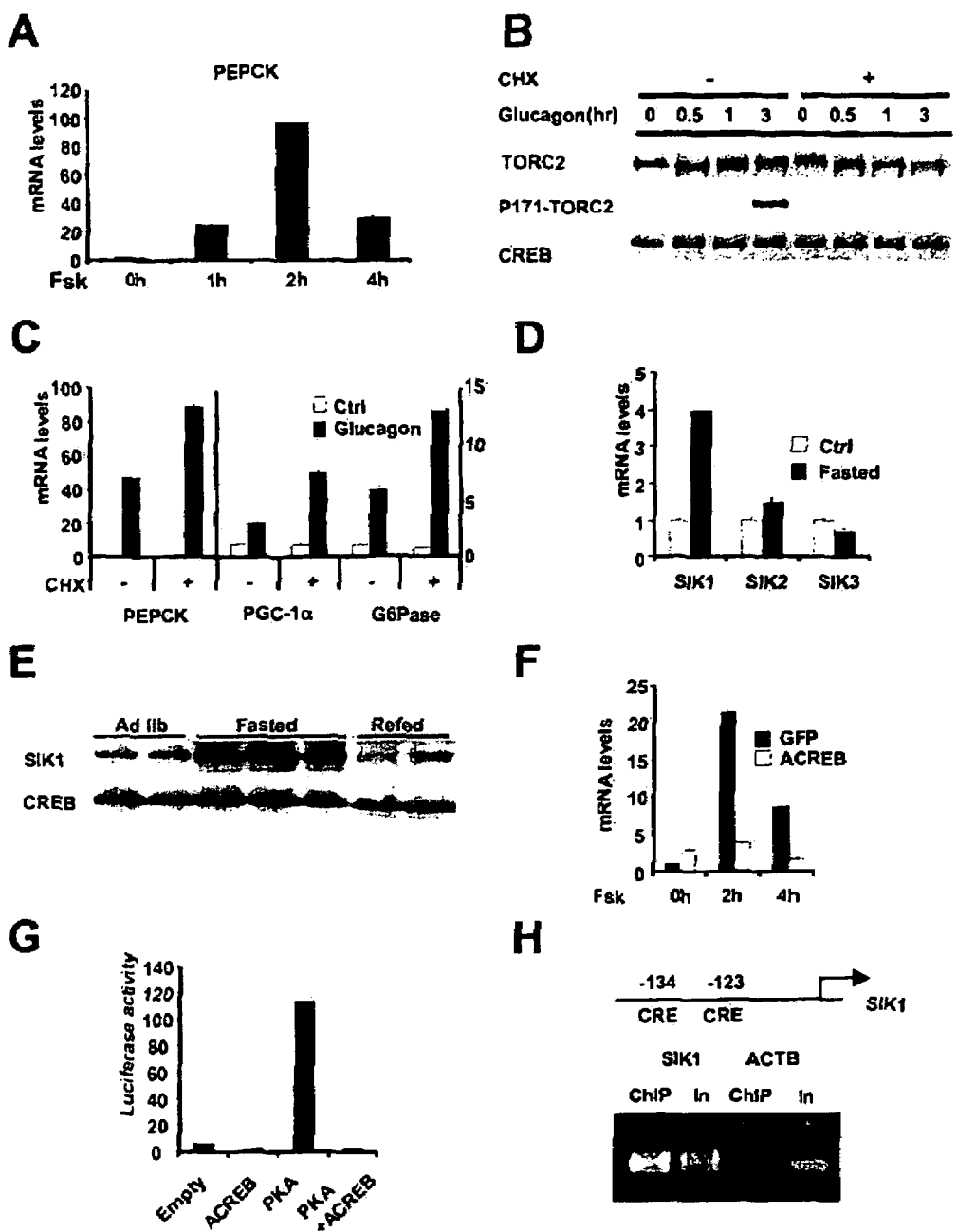
FIGS. 18A-18H illustrate that the induction of the AMP kinase family member SIK1 by CREB during fasting attenuates the gluconeogenic program. Specifically.

Like other signaling pathways, cAMP stimulates gluconeogenic gene expression with burst-attenuation kinetics (see Sasaki et al., 1984). Following exposure of primary hepatocytes to Forskolin, PEPCK mRNA levels became maximal after 2 hours, returning to near baseline after 4 hours (see FIG. 18A). Consistent with this profile, TORC2 phosphorylation at Ser171 was strongly induced 3 hours after glucagon stimulation in primary rat hepatocytes (see FIG. 18B). Pre-treatment with protein synthesis inhibitor cycloheximide (CHX) blocked phosphorylation of TORC2 at Ser171 by glucagon at 3 hours, suggesting that fasting signals promote the synthesis of an activity which in turn feeds back to shut down the CREB:TORC pathway (see FIG. 18B). Consistent with this, CHX pre-treatment potentiated gluconeogenic gene expression in primary rat hepatocytes exposed to glucagon 2-3 fold (see FIG. 18C).

Based on the ability of CHX to disrupt TORC2 Ser171 phosphorylation, it was hypothesized that glucagon induces the expression of an inhibitory kinase during the attenuation period. In previous studies, the SIK family of AMP kinases has been found to associate with and to phosphorylate TORC2 at Ser171 (see Screaton et al., 2004), part of an optimal consensus site for AMPK (AMP-activated protein kinase) family members (LNRTSSDSAL; SEQ ID NO:9). Indeed, fasting induced SIK1 mRNA and protein levels in liver 4-fold relative to feeding conditions, whereas expression of other SIK family members (SIK2 and SIK3) was unaffected (see FIGS. 18D and 18E). Exposure of primary rat hepatocytes to FSK strongly induced SIK1 mRNA levels 20-fold, and these effects were disrupted by Ad-A-CREB (see FIG. 18F). Notably, FSK had no effect on mRNA levels for any of the 12 AMPK family members by gene profiling assay of primary mouse hepatocytes, indicating that these effects are indeed specific for SIK1.

Examination of the SIK1 gene promoter revealed two consensus cAMP responsive promoter elements in rat, mouse, and human orthologs, consistent with the proposal that SIK1 is a direct target for CREB induction. In transient assays of HepG2 hepatocytes, PKA stimulated SIK1 promoter activity about 20-fold; these effects were disrupted by co-expression of A-CREB (see FIG. 18G). Indeed, CREB was found to occupy the SIK1 promoter in ChIP assays of mouse hepatocytes, consistent with the proposed direct role for CREB in this process (see FIG. 18H).

Figure 19:
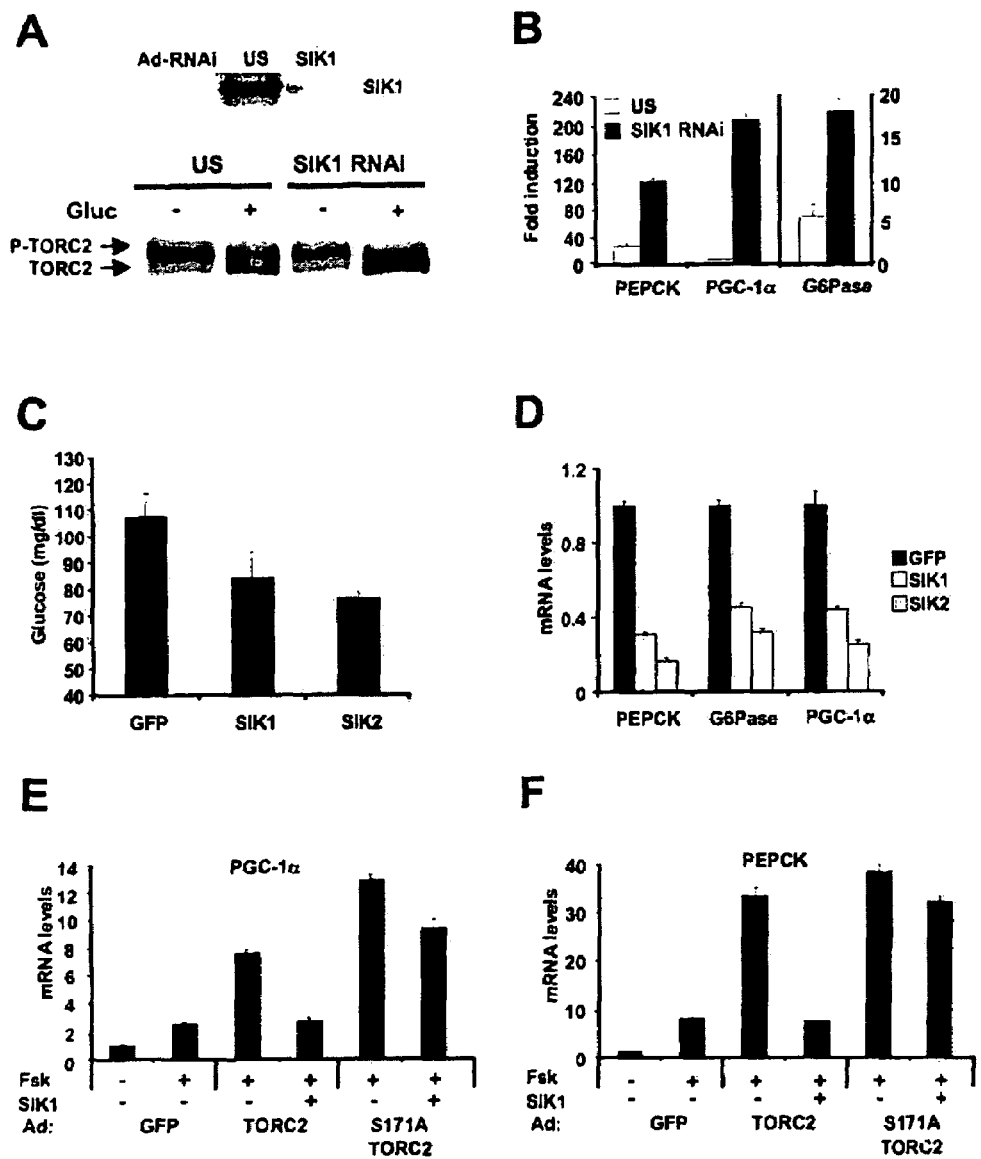
FIGS. 19A-19F demonstrate that SIKs inhibit hepatic gluconeogenesis via phosphorylation of TORC2 at Ser171. Specifically, FIG. 19A, top, presents a Western blot showing the effect of US and SIK1 RNAi adenoviruses on the levels of SIK1 protein in rat hepatocytes.

Having seen that glucagon triggers hepatic expression of SIK1 during fasting, it was next considered whether this kinase functions as part of an auto-regulatory loop in attenuating the gluconeogenic program. Using a SIK1 RNAi adenovirus that reduced SIK1 expression about 75%, it was found that glucagon stimulated TORC2 dephosphorylation to a far greater extent in SIK1 knockdown compared to control cells (see FIG. 19A). Knockdown of SIK1 also enhanced gluconeogenic gene expression; mRNA levels for PGC-1α were increased 70-fold in SIK1 deficient cells (see FIG. 1 9B). Conversely, over-expression of SIK1 induced Ser171 phosphorylation and blocked induction of the PEPCK promoter by TORC2 in hepatocytes exposed to FSK. However, SIK1 had no effect on the ability of PGC-1 to stimulate transcription from a PPARA target gene (Acyl CoA oxidase (AOX)), which is not consistent with the existence of a general inhibitory effect of this kinase on hepatocyte gene expression.

The role of SIK1 on fasting glucose metabolism was further evaluated using Ad-SIK1. Relative to control littermates, mice injected with either Ad-SIK1 or Ad-SIK2 exhibited fasting hypoglycemia and reduced gluconeogenic gene expression (see FIGS. 19C and 19D). Although the ability of Ad-SIK1 to block hepatic glucose output in this setting could reflect an unanticipated induction of the insulin pathway, fasting insulin levels were actually lower in SIK1 or SIK2 expressing mice, compared to control mice; hepatic insulin signaling was comparable in primary hepatocytes infected with a SIK1 adenovinus, as revealed by Western blot assay of phospho (Ser473) Akt levels following 30 min exposure to insulin (100 nM).

To evaluate whether SIK1 inhibits the gluconeogenic program via TORC2 phosphorylation, an adenovirus expressing Ser171Ala TORC2 was prepared. Following infection into primary rat hepatocytes, adenoviral wild-type and mutant Ser171Ala TORC2 polypeptides were expressed at comparable levels and had similar effects on PEPCK and PGC-1α gene expression (see FIGS. 19E and 19F). Over-expression of SIK1 blocked wild-type TORC2 activity almost completely; but the mutant Ser171 Ala TORC2 protein was refractory to SIK1 inhibition, demonstrating the importance of Ser171 phosphorylation for disruption of the gluconeogenic program by this kinase (see FIGS. 19E and 19F).

Activation of the AMPK (AMP-activated protein kinase) pathway in liver has been shown to block expression of gluconeogenic genes, although the relevant targets for this inhibition have remained elusive (see Lockhead et al., 2000 and Yamauchi et al., 2002). By contrast with SIK, ATP depletion appears to be uniquely sensed by AMPK, the founding member of this family (see Sakamoto et al., 2004; Lizcano et al., 2004; Bananjee et al., 2004; and Radzuik et al., 2003). The presence of a consensus AMPK phosphorylation site (Ser171) that modulates TORC2 activity in liver prompted examination of whether AMPK inhibits gluconeogenesis via phosphorylation of TORC2 in response to ATP depletion. Activated AMPK phosphorylated wild-type, but not Ser171Ala mutant GST-TORC2 (161-181) peptide in vitro (see FIG. 20A). Phosphorylation of TORC by AMPK was comparable to an optimal AMPK peptide substrate (SAMS (see Lizcano et al., 2004) and was induced by addition of AMP. Indeed, selective activation of cellular AMPK by exposure of primary hepatocytes to the AMP analogue 5-aminoimidazole-4-carboxamide riboside (AICAR) triggered robust phosphorylation of endogenous TORC2 even in the presence of FSK (see FIG. 20B).

Based on its ability to promote Ser171 phosphorylation, AMPK might be expected to inhibit nuclear entry of TORC2 in cells exposed to FSK. Using primary rat hepatocytes infected with adenoviruses expressing either wild-type or Ser171Ala mutant TORC2 polypeptides, it was found that FSK triggered translocation of wild-type TORC2 (see FIG. 20C). Confirming the pivotal role of Ser171 in this regard, mutant Ser171Ala TORC2 remained constitutively nuclear under both conditions. Treatment with AICAR inhibited nuclear entry of wild-type, but not SerAla171 TORC2, in cells exposed to FSK; and adenoviral expression of SIK1 in these cells similarly blocked TORC2 nuclear entry in a Ser171 dependent manner (see FIG. 20C).

Figure 20:
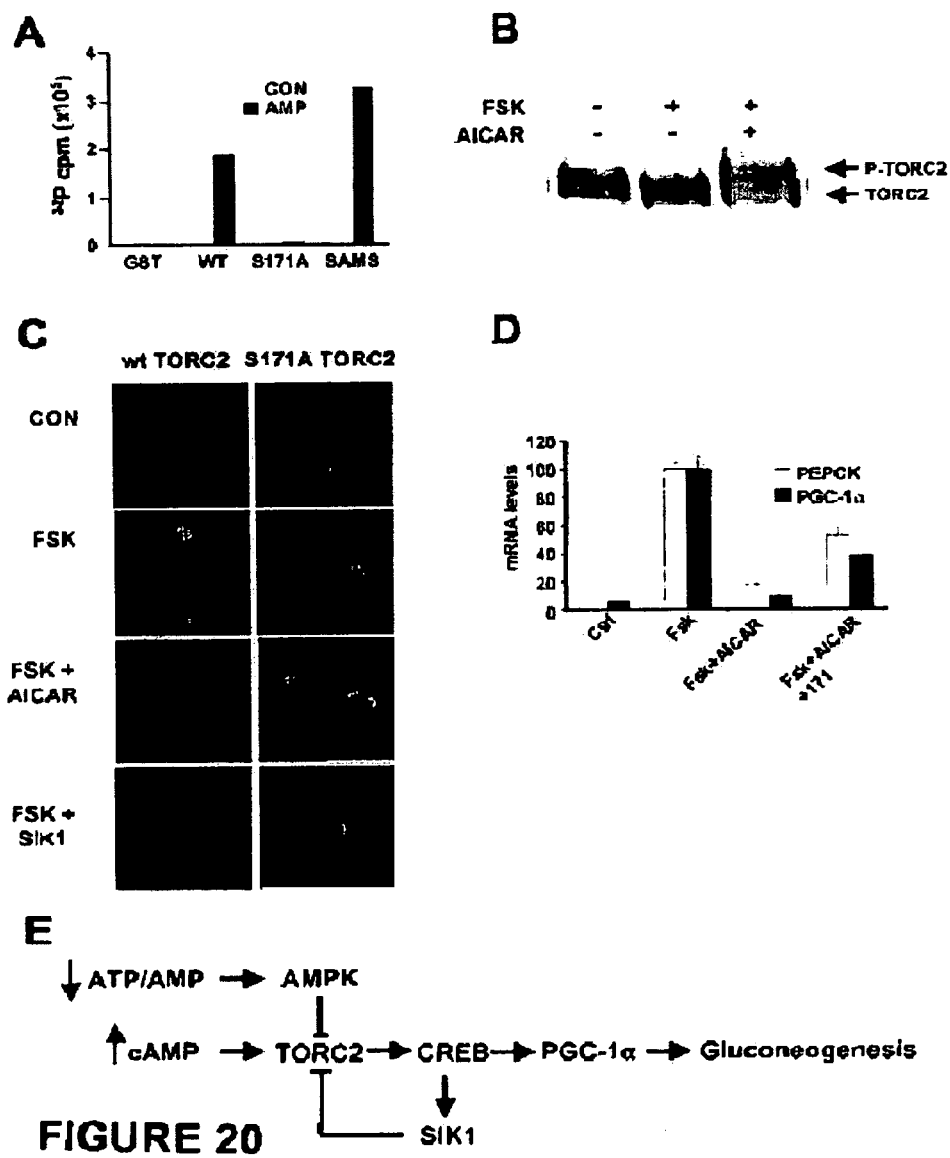
FIGS. 20A-20E demonstrate that the energy sensing AMPK (AMP-activated protein kinase) pathway regulates TORC2 activity in liver. Specifically.

Activation of AMPK (AMP-activated protein kinase) by AICAR in primary hepatocytes to AICAR blocked induction of PEPCK and PGC-1α genes in response to FSK (see FIG. 20D). If the AMPK pathway inhibits the gluconeogenic program via TORC2, then a phosphorylation defective Ser171 Ala mutant TORC2 would be predicted to rescue the inhibitory effects of AICAR on these genes. Consistent with this prediction, mutant Ad-TORC (Ser171Ala) rescued expression of PEPCK and PGC-1α in the presence of AICAR inhibitor, demonstrating the importance of Ser171 in mediating inhibitory effects of AMPK on gluconeogenic genes (see FIG. 20D).

The results described herein are consistent with a mechanism of action whereby TORC2 functions as a master switch for modulation of gluconeogenic genes in response to nutritional and stress signals (see FIG. 20E). TORC2 activity is tightly regulated during fasting by SIK1, which forms part of an autoregulatory loop that attenuates the gluconeogenic program by phosphorylating TORC2 at Ser171 and promoting its export to the cytoplasm. TORC2 is additionally regulated by AMPK; activation of AMPK in response to an AMP analog disrupted hepatic gluconeogenic gene expression in part via Ser171 phosphorylation of TORC2. Indeed, a number of adipokines such as adiponectin (see Yamauchi et al., 2002) and resistin (see Bananjee et al., 2004) have been shown to modulate hepatic gluconeogenesis via an AMPK dependent mechanism; the results presented herein provide a regulatory mechanism to explain these effects. For example, metformin, a compound that activates AMPK (see Radzuik et al., 2003), has been widely used for treatment of type II diabetes due to its effects in blocking hepatic gluconeogenesis and in stimulating glucose uptake in muscle (see also Bergeron et al., 2001). Other compounds that enhance TORC2 phosphorylation in liver would be expected to provide similar therapeutic benefit for individuals with insulin resistance.

The invention has been described in detail with reference to preferred embodiments thereof. However, it will be appreciated that those skilled in the art, upon consideration of this disclosure, may make modification and improvements within the spirit and scope of the invention as set forth in the following claims.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

REFERENCES

Ahn, S. et al. A dominant negative inhibitor of CREB reveals that it is a general mediator stimulus-dependent transcription of c-fos. *Molec. Cell. Biol.* 18, 967-977 (1998).

Al-Uzri, A., Stablein, D. M., and Cohn, A. R. (2001). Post-transplant diabetes mellitus in pediatric renal transplant recipients: a report of the North American Pediatric Renal Transplant Cooperative Study (NAPRTCS). Transplantation 72, 1020-1024.

Ararnburu, J., Garcia-Cozar, F., Raghavan, A,, Okamura, H., Rao, A,, and Hogan, P. G. (1998). Selective inhibition of NFAT activation by a peptide spanning the calcineurin targeting site of NFAT. Mol Cell 1, 627-637.

Arias, J., Alberts, A., Brindle, P., Claret, F., Smeal, T., Karin. M., Feramisco, J., and Montminy, M. (1994). Activation of CAMP and mitogen responsive genes relies on a common nuclear factor. Nature 370,226-228.

Asahara, H., Santoso, B., Du, K., Cole, P., and Montminy, M. (2001). Chromatin Dependent Cooperativity Between Constitutive and Inducible Activation Domains in CREB. Molecular and Cellular Biology 21, 7892-7900.

Banenjee, R. R. et al. Regulation of fasted blood glucose by resistin. Science 303, 1195-8 (2004).

Bergeron, R. et al. Effect of 5-aminoimidazole-4-canboxamide-1-beta-Dribofuranoside infusion on in vivo glucose and lipid metabolism in lean and obese Zucker rats. *Diabetes* 50, 1076-82 (2001).

Bittinger, M. A. et al. Activation of cAMP response element-mediated gene expression by regulated nuclear transport of TORC proteins. Curr Biol 14, 2156-61(2004).

Bonni, A,, Ginty, D., Dudek, H., and Greenberg, M. (1995a). Serine 133 phosphorylated CREB Induces Transcription via a Cooperative Mechanism That May confer Specificity to Neurotrophin Signals. Molecular and Cellular Neurosciences 6, 168-183.

Bonni, A,, Ginty, D. D., Dudek, H., and Greenberg, M. E. (1995b). Serine 133-phosphorylated CREB induces transcription via a cooperative mechanism that may confer specificity to neurotrophin signals. Mol Cell Neurosci 6, 168-183.

Brunet, A,, Bonni, A., Zigmond, M. J., Lin. M. Z., Juo, P., Hu, L. S., Anderson, M. J., Arden, K. C., Blenis, J., and Greenberg, M. E. (1999). Akt promotes cell survival by phosphorylating and inhibiting a Forkhead transcription factor. Cell 96, 857-868.

Carling, D. (2004). The AMP-activated protein kinase cascade—a unifying system for energy control. Trends Biochem Sci 29, 18-24.

Chen, M. S., Ryan, C. E., and Piwnica-Worms, H. (2003). Chk1 kinase negatively regulates mitotic function of Cdc25A phosphatase through 14-3-3 binding. Mol Cell Biol 23,7488-7497.

Chow, C. W., and Davis, R. J. (2000). Integration of calcium and cyclic AMP signaling pathways by 14-3-3. Mol Cell Biol20,702-712.

Chrivia, J. C., Kwok, R. P., Lamb, N., Hagiwara, M., Montminy. M. R., and Goodman, R. H. (1993). Phosphorylated CREB binds specifically to the nuclear protein CBP. Nature 365, 855-859.

Conkright, M. D., Canettieri, G., Screaton, R., Guzman, E., Miraglia, L., Hogenesch, J. B., and Montminy, M. (2003a). TORCs: transducers of regulated CREB activity. Mol Cell 12,413-423.

Conkright, M. D., Guzman, E., Flechner, L., Su, A. I., Hogenesch, J., and Montminy, M. (2003b). Genome Wide Analysis of CREB Target Genes Reveals A Core Promoter Requirement for CAMP Responsiveness. Mol Cell 11, 1101-1108.

Crabtree, G. R., and Olson, E. N. (2002). NFAT signaling: choreographing the social lives of cells. Cell 109 Suppl, S67-79.

Doi, J., Takemori, H., Lin, X. Z., Horike, N., Katoh, Y., and Okamoto, M. (2002). Saltinducible kinase represses cAMP-dependent protein kinase-mediated activation of human cholesterol side chain cleavage cytochrome P450 promoter through the CREB basic leucine zipper domain. J Biol Chem 277, 15629-15637.

Dougherty, M. and Morrison, D. (2004). Unlocking the code of 14-3-3. J Cell Science 117:1875-1884.

Durocher, D., Taylor, I. A,, Sarbassova, D., Haire, L. F., Westcon, S. L., Jackson, S. P., Smerdon, S. J., and Yaffe, M. B. (2000). The molecular basis of FHA domain:phosphopeptide binding specificity and implications for phospho-dependent signaling mechanisms. Mol Cell 6, 1169-1182.

Enlund, F., Behhoudi, A,, Andren, Y., Oberg, C., Lendahl, U., Mark, J., and Stenman, G. (2004). Altered Notch signaling resulting from expression of a WAMTPI-MAML2 gene fusion in mucoepidermoid carcinomas and benign Warthin's tumors. Exp Cell Res 292, 21-28.

Filler, G., Neuschulz, I., Vollmer, I., Amendt, P., and Hocher, B. (2000). Tacrolimus reversibly reduces insulin secretion in paediatric renal transplant recipients. Nephrol Dial Transplant 15, 867-871.

Gonzalez, G. A,, and Montminy, M. R. (1989). Cyclic AMP stimulates somatostatin gene transcription by phosphorylation of CREB at Serine 133. Cell 59, 675-680.

Goodman, R. H., and Smolik, S. (2000). CBPlp3OO in cell growth, transformation, and development. Genes Dev 14, 1553-1577.

Hall, R. K. & Granner, D. K. Insulin regulates expression of metabolic genes through divergent signaling pathways. JBasic Clin Physiol Pharmacol 10, 119-33 (1999).

Hanson, R. W. & Reshef, L. Regulation of phosphoenolpyruvate carboxykinase (GTP) gene expression. Annu Rev Biochem 66, 581-611(1997).

Herzig, S. et al. CREB Regulates Hepatic Gluconeogenesis via the Co-activator PGC-1. *Nature* 413, 179-183 (2001).

Hogan, P. G., Chen, L., Nardone, J., and Rao, A. (2003). Transcriptional regulation by calcium, calcineurin, and NFAT. Genes Dev 17,2205-2232.

Horike, N., Takemori, H., Katoh, Y., Doi, J., Min, L., Asano, T., Sun, X., Yamamoto, H., Kasayama S., Muraoka, M., Nanaka, Y., Okamoto, M., (2003).Adipose-specific expression, phosphorylation of Ser$^{794}$ in insulin receptor substrate-1, and activation in diabetic animals of salt-induced kinase-2. J. Biol. Chem. 278:18440-7.

Hui, H., Nourparvar, A., Zhao, X. and Perfetti, R. (2003). Glucagon-like peptide-1 inhibits apoptosis of insulin-secreting cells via a cyclic 5'-adenosine monophosphatedependent protein kinase A- and a phosphatidylinositol3-kinase-dependent pathway. Endocrinology 144, 1444-1455.

Iourgenko, V., Zhang, W., Mickanin, C., Daly, I., Jiang, C., Hexham, J. M., Orth, A. P., Miraglia, L., Meltzer, J., Garza. D., et aL (2003). Identification of a family of cAMP response element-binding protein coactivators by genome-scale functional analysis in mammalian cells. Proc Natl Acad Sci U S A 100, 12 147-52.

Jhala, U. S., Canettieri, G., Screaton, R. A,, Kulkami, R. N., Krajewski, S., Reed, J., Walker, J., Lin, X., White, M. and Montminy, M. (2003). cAMP promotes pancreatic beta-cell survival via CREB-mediated induction of LRS2. Genes Dev 17, 1575-1580.

Kahn, B. B., Alquier, T., Carling, D. & Hardie, D. G. AMP-activated protein kinase: Ancient energy gauge provides clues to modern understanding of metabolism. *Cell Metabolism* 1, 15-25 (2005).

Kasper, L. H., Boussouar, F., Ney, P. A,, Jackson, C. W., Rehg, J., van Deursen, J. M., and Brindle, P. K. (2002). A transcription-factor-binding surface of coactivator p300 is required for haematopoiesis. Nature 41 9, 738-743.

Katoh, Y. et al., (2004). Salt-inducible kinase (SIK) isoforms: their involvement in steroidogenesis and adipogenesis. Mol Cell Endocrinol 217:109-12.

Katoh, Y. et al. Salt-inducible kinase-1 represses cAMP response element-binding protein activity both in the nucleus and in the cytoplasm. *Eur J Biochem* 271, 4307-19 (2004).

Koo, S. H. et al. PGC-1 promotes insulin resistance in liver through PPAR-alphadependent induction of TRB-3. *Nat Med* (2004).

Koo, S. H., et al. The CREB coactivator TORC2 is a key regulator of fasting glucose metabolism. Nature 43 7, 1109-1114 (2005).

Kornhauser, J. M., Cowan, C. W., Shaywitz, A. J., Dolmetsch. R. E., Griff~th, E. C., Hu, L.

S., Haddad, C., Xia, Z., and Greenberg, M. E. (2002). CREB transcriptional activity in neurons is regulated by multiple, calcium-specific phosphorylation events. Neuron 34, 221-233.

Kwok, R., Lundblad, J., Chrivia, J., Richards, J., Bachinger, H., Brennan, R., Roberts, S., Green, M., and Goodman, R. (1994). Nuclear protein CBP is a coactivator for the transcription factor CREB. Nature 370, 223-226.

Lemaigre, F. P., Ace, C. I., and Green, M. R. (1993). The cAMP response element binding protein, CREB, is a potent inhibitor of diverse transcriptional activators. Nucleic Acids Res 21,2907-291 1.

Lin, J. et al. Defects in adaptive energy metabolism with CNS-linked hyperactivity in PGC-1 alpha null mice. Cell 119, 12 1-35 (2004).

Link, A. J., Eng, J., Schieltz, D. M., Carmack, E., Mize, G. J., Morris, D. R., Garvik, B. M., and Yates, J. R., 3rd (1999). Direct analysis of protein complexes using mass spectrometry. Nat Biotechnol 17,676-682.

Lizcano, J. M., Goransson, O., Toth, R., Deak, M., Morrice, N. A., Boudeau, J., Hawley, S.

A,, Udd, L., Makela, T. P., Hardie, D. G., and Alessi, D. R. (2004). LKB1 is a master kinase that activates 13 kinases of the AMPK subfamily, including MARWAR-]. Embo J 23,833-843.

Lochhead, P. A., Salt, I. P., Walker, K. S., Hardie, D. G. & Sutherland, C. 5-aminoimidazole-4-carboxamide riboside mimics the effects of insulin on the expression of the 2 key gluconeogenic genes PEPCK and glucose-6-phosphatase. Diabetes 49, 896-903 (2000). MacCoss, M. J., McDonald, W. H., Saraf, A,, Sadygov, R., Clark, J. M., Tasto, J. J., Gould, K. L., Wolters, D., Washbum, M., Weiss, A,, et al. (2002). Shotgun identification of protein modifications from protein complexes and lens tissue. Proc Natl Acad Sci U S A 99, 7900-7905.

Mayr, B., and Montminy, M. (2001). Tanscriptional Regulation by the Phosphorylation Dependent Factor CREB. Nature Reviews-Molecular Cell Biology 2, 599-609.

Newgard, C. B., and McGarry, J. D. (1995). Metabolic coupling factors in pancreatic beta-cell signal hansduction. Annu Rev Biochem 64,689-719.

Newman, J. R., and Keating, A. E. (2003). Comprehensive identification of human bZIP interactions with coiled-coil arrays. Science 300,2097-210 I.

Okamoto, M., Takemori, H., and Katoh, Y. (2004). Salt-inducible kinase in steroidogenesis and adipogenesis. Trends Endocrinol Metab 15,21-26.

Okamura, H., Arambum, J., Garcia-Rodriguez, C., Viola, J. P., Raghavan, A, Tahiliani, M., Zhang, X., Qin, J., Hogan, P. G., and Rao, A. (2000). Concerted dephosphorylation of the transcription factor NFAT1 induces a conformational switch that regulates transcriptional activity. Mol Cell 6, 539-550.

Parker, D., Jhala, U., Radhakrishnan, I., Yaffe, M., Reyes, C., Shulman, A., Cantley, L., Wright, P., and Montminy, M. (1998). Analysis of an Activator:Coactivator Complex Reveals an Essential Role for Secondary Structure in Transcriptional Activation. Molecular Cell 2,353-359.

Radhakrishnan, I., G.C.Perez-Alvarado, Parker, D., Dyson, H. J., Montminy, M., and Wright, P. E. (1997). Solution structure of the KIX domain of CBP bound to the transactivation domain of CREB: a model for activator-coactivator interactions. Cell 91, 741-752.

Radziuk, J., Bailey, C. J., Wiemsperger, N. F. & Yudkin, J. S. Metformin and its liver targets in the treatment of type 2 diabetes. *Curr Drug Targets Immune Endocr Metabol Disord* 3, 151-69 (2003).

Sakamoto, K., Goransson, O., Handie, D. G. & Alessi, D. R. Activity of LKB 1 and AMIPK-related kinases in skeletal muscle: effects of contraction, phenformin, and AICAR. *Am J Physiol Endocrinol Metab* 287, E310-7 (2004).

Saltiel, A. & Kahn, C. R. Insulin signalling and the regulation of glucose and lipid metabolism. *Nature* 414, 799-806 (2001).

Sasaki, K. et al. Multihormonal regulation of phosphoenolpyruvate carboxykinase gene transcription. *J Biol Chem* 259, 15242-15251 (1984).

Schwaninger, M., Blume, R., Kruger, M., Lux, G., Oetjen, E., and Knepel, W. (1995). Involvement of the Ca(2+)-dependent phosphatase calcineurin in gene transcription that is stimulated by cAMP through cAMP response elements. J Biol Chem 270, 8860-8866.

Screaton, R. A. et al. The CREB coactivator TORC2 functions as a calcium- and cAMP-sensitive coincidence detector. *Cell* 119, 61-74 (2004).

Shaw, R. J., Kosmatka, M., Bardeesy, N., Hurley, R. L., Witters, L. A., DePinho, R. A., and Cantley, L. C. (2004). The tumor suppressor LKB1 kinase directly activates AMP activated kinase and regulates apoptosis in response to energy stress. Proc Natl Acad Sci U S A 101,3329-3335.

Shaywitz, A. J., and Greenberg, M. E. (1999). CREB: A Stimulus-Induced Transcription Factor Activated by A Diverse Array of Extracellular Signals. Annu Rev Biochem 68, 821-861.

Sheng, M., Thompson, M. A., and Greenberg, M. E. (1991). CREB: A Ca-Regulated Transcription Factor Phosphorylated by Calmodulin-Dependent Kinases. Science 252, 1427-1430.

Tabb, D. L., MacDonald, W. H., and Yates, J. R. (2002). DTASelect and Contrast: tools for assembling and comparing protein identifications from shotgun proteomics. Journal of Proteome Research 1,21-26.

Tonon, G., Modi, S., Wu, L., Kubo, A., Coxon, A. B., Komiya, T., O'Neil, K., Stover, K., El-Naggar, A, Griffin, J. D., et al. (2003). t(11;19)(q21;p13) translocation in mucoepidermoid carcinoma creates a novel fusion product that disrupts a Notch signaling pathway. Nat Genet 33,208-213.

Voon, J. et al. Control of hepatic gluconeogenesis through the transcriptional coactivator PGC-1. *Nature* 413, 13 1-138 (2001).

Woods, A, Johnstone, S. R., Dickerson, K., Leiper, F. C., Fryer, L. G., Neumann, D., Schlattner, U., Wallimann, T., Carlson, M., and Carling, D. (2003). LKB1 is the upstream kinase in the AMP-activated protein kinase cascade. Curr Biol 13,2004-2008.

Yamauchi, T. et al. Adiponectin stimulates glucose utilization and fatty-acid oxidation by activating AMP-activated protein kinase. *Nat Med* 8, 1288-95 (2002).

Sequence Listing
SEQ ID NO:1
 PLARTLSVAGLPGKK
SEQ ID NO:2
 248-PGINIF
SEQ ID NO:3
 PXIXIT
SEQ ID NO:4
 RXXXpSXP
SEQ ID NO:5
 GGGGCAGTTGTTTAGACTGCC
SEQ ID NO:6
 GGGCACTTGAGTGAAAACGAGG
SEQ ID NO:7
 LXB(S/T)XSXXXL
SEQ ID NO:8
 166-LNRTSSDSAL
SEQ ID NO:9
 LNRTSSDSAL

---

The invention claimed is:

1. A method of screening test compounds to determine whether such compounds affect the level of phosphorylation of a Transducer Of Regulated CREB (TORC), said method comprising determining the effect of test compound on the level of phosphorylation of TORC.

2. The method of claim 1 wherein said test compound enhances the level of phosphorylation of TORC.

3. The method of claim 1 wherein said test compound reduces the level of phosphorylation of TORC.

4. The method of claim 1 wherein said method is carried out in the further presence of calcineurin.

* * * * *

SEQUENCE LISTING

<160> NUMBER OF SEQ ID NOS: 53

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Pro Leu Ala Arg Thr Leu Ser Val Ala Gly Leu Pro Gly Lys Lys
 1               5                   10                  15

<210> SEQ ID NO 2
<211> LENGTH: 6
<212> TYPE: PRT
<213> ORGANISM: Mus musculus

```
<400> SEQUENCE: 2

Pro Gly Ile Asn Ile Phe
 1               5

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Variable amino acid
<220> FEATURE:
<221> NAME/KEY: MOD_RES
<222> LOCATION: (4)
<223> OTHER INFORMATION: Variable amino acid

<400> SEQUENCE: 3

Pro Xaa Ile Xaa Ile Thr
 1               5

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(4)
<223> OTHER INFORMATION: Variable amino acid
<220> FEATURE:
<221> NAME/KEY: MOD_RES
<222> LOCATION: (5)
<223> OTHER INFORMATION: Phospho-Ser
<220> FEATURE:
<221> NAME/KEY: MOD_RES
<222> LOCATION: (6)
<223> OTHER INFORMATION: Variable amino acid

<400> SEQUENCE: 4

Arg Xaa Xaa Xaa Ser Xaa Pro
 1               5

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 5
ggggcagttg tttagactgc c                                         21

<210> SEQ ID NO 6
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
gggcacttga gtgaaaacga gg                                        22
```

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence: Synthetic peptide
<220> FEATURE:
<221> NAME/KEY: MOD_RES
<222> LOCATION: (2)
<223> OTHER INFORMATION: Variable amino acid
<220> FEATURE:
<221> NAME/KEY: MOD_RES
<222> LOCATION: (3)
<223> OTHER INFORMATION: Basic amino acid
<220> FEATURE:
<221> NAME/KEY: MOD_RES
<222> LOCATION: (4)
<223> OTHER INFORMATION: Ser or Thr
<220> FEATURE:
<221> NAME/KEY: MOD_RES
<222> LOCATION: (5)
<223> OTHER INFORMATION: Variable amino acid
<220> FEATURE:
<221> NAME/KEY: MOD_RES
<222> LOCATION: (7)..(9)
<223> OTHER INFORMATION: Variable amino acid

<400> SEQUENCE: 7

Leu Xaa Xaa Xaa Xaa Ser Xaa Xaa Xaa Leu
 1               5                  10

<210> SEQ ID NO 8
<211> LENGTH: 10
<212> TYPE: PRT
<213> ORGANISM: Mus musculus

<400> SEQUENCE: 8

Leu Asn Arg Thr Ser Ser Asp Ser Ala Leu
 1               5                  10

<210> SEQ ID NO 9
<211> LENGTH: 10
<212> TYPE: PRT
<213> ORGANISM: Artificial Sequence
<220> FEATURE:
<223> OTHER INFORMATION: Description of Artificial Sequence: Synthetic peptide

<400> SEQUENCE: 9

Leu Asn Arg Thr Ser Ser Asp Ser Ala Leu
 1               5                  10

<210> SEQ ID NO 10
<211> LENGTH: 17
<212> TYPE: PRT
<213> ORGANISM: Homo sapiens

<400> SEQUENCE: 10

Thr Gly Gly Ser Leu Pro Asp Leu Thr Asn Ile His Phe Pro Ser Pro
 1               5                  10                  15

Leu

<210> SEQ ID NO 11
<211> LENGTH: 17
<212> TYPE: PRT
<213> ORGANISM: Homo sapiens

```
<400> SEQUENCE: 11

Thr Gly Gly Ser Leu Pro Asp Leu Thr Asn Leu His Phe Pro Pro Pro
 1               5                  10                  15
Leu

<210> SEQ ID NO 12
<211> LENGTH: 17
<212> TYPE: PRT
<213> ORGANISM: Homo sapiens

<400> SEQUENCE: 12

Thr Gly Gly Ser Leu Pro Asp Leu Thr Asn Leu His Tyr Ser Thr Pro
 1               5                  10                  15
Leu

<210> SEQ ID NO 13
<211> LENGTH: 18
<212> TYPE: PRT
<213> ORGANISM: Homo sapiens

<400> SEQUENCE: 13

Ser Thr Gly Asn Leu Ala Ala Asn Leu Thr His Leu Gly Ile Gly Gly
 1               5                  10                  15
Ala Gly

<210> SEQ ID NO 14
<211> LENGTH: 18
<212> TYPE: PRT
<213> ORGANISM: Homo sapiens

<400> SEQUENCE: 14

Ser Thr Thr Asn Leu Thr His Thr Met Thr His Leu Gly Ile Ser Gly
 1               5                  10                  15
Gly Leu

<210> SEQ ID NO 15
<211> LENGTH: 18
<212> TYPE: PRT
<213> ORGANISM: Homo sapiens

<400> SEQUENCE: 15

Ser Val Asn Asn Ile Pro Ala Ala Met Thr His Leu Gly Ile Arg Ser
 1               5                  10                  15
Ser Ser

<210> SEQ ID NO 16
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(4)
<223> OTHER INFORMATION: Variable amino acid and this region may
      encompass 1 to 3 residues
<220> FEATURE:
<221> NAME/KEY: MOD_RES
<222> LOCATION: (6)..(8)
<223> OTHER INFORMATION: Variable amino acid and this region may
      encompass 2 or 3 residues
<220> FEATURE:
<221> NAME/KEY: MOD_RES
```

```
<222> LOCATION: (10)
<223> OTHER INFORMATION: Variable amino acid

<400> SEQUENCE: 16

Leu Xaa Xaa Xaa Leu Xaa Xaa Xaa Leu Xaa Leu
 1               5                  10

<210> SEQ ID NO 17
<211> LENGTH: 13
<212> TYPE: PRT
<213> ORGANISM: Mus musculus

<400> SEQUENCE: 17

Ser Ser His Tyr Gly Gly Ser Leu Pro Asn Val Asn Gln
 1               5                  10

<210> SEQ ID NO 18
<211> LENGTH: 13
<212> TYPE: PRT
<213> ORGANISM: Mus musculus

<400> SEQUENCE: 18

Phe Gln Ser Pro Leu His Ser Pro Leu Asp Ser Ser Arg
 1               5                  10

<210> SEQ ID NO 19
<211> LENGTH: 13
<212> TYPE: PRT
<213> ORGANISM: Mus musculus

<400> SEQUENCE: 19

Tyr Ser Pro Ala Tyr Leu Ser Pro Pro Pro Glu Ser Gly
 1               5                  10

<210> SEQ ID NO 20
<211> LENGTH: 13
<212> TYPE: PRT
<213> ORGANISM: Mus musculus

<400> SEQUENCE: 20

Ser Leu Ser Gly Gly Asn Ser Thr Thr Asn Leu Thr His
 1               5                  10

<210> SEQ ID NO 21
<211> LENGTH: 13
<212> TYPE: PRT
<213> ORGANISM: Mus musculus

<400> SEQUENCE: 21

Gln Leu Gln Gly Ser His Ser His Pro Ser Leu Pro Ala
 1               5                  10

<210> SEQ ID NO 22
<211> LENGTH: 13
<212> TYPE: PRT
<213> ORGANISM: Mus musculus

<400> SEQUENCE: 22

Leu Gly His Pro Ser Leu Ser Ala Pro Ala Leu Ser Ser
 1               5                  10

<210> SEQ ID NO 23
<211> LENGTH: 13
<212> TYPE: PRT
<213> ORGANISM: Mus musculus
```

```
<400> SEQUENCE: 23

His Arg Arg Val Pro Leu Ser Pro Leu Ser Leu Pro Ala
 1               5                  10

<210> SEQ ID NO 24
<211> LENGTH: 13
<212> TYPE: PRT
<213> ORGANISM: Mus musculus

<400> SEQUENCE: 24

Gln Leu Pro Lys Gln Phe Ser Pro Thr Met Ser Pro Thr
 1               5                  10

<210> SEQ ID NO 25
<211> LENGTH: 13
<212> TYPE: PRT
<213> ORGANISM: Mus musculus

<400> SEQUENCE: 25

Leu Pro Pro Tyr Pro Tyr Ser Pro Pro Ser Leu Val Ile
 1               5                  10

<210> SEQ ID NO 26
<211> LENGTH: 13
<212> TYPE: PRT
<213> ORGANISM: Mus musculus

<400> SEQUENCE: 26

Tyr Pro Tyr Ser Pro Pro Ser Leu Val Ile Pro Thr His
 1               5                  10

<210> SEQ ID NO 27
<211> LENGTH: 13
<212> TYPE: PRT
<213> ORGANISM: Mus musculus

<400> SEQUENCE: 27

Ala Leu Asn Arg Thr Ser Ser Asp Ser Ala Leu His Thr
 1               5                  10

<210> SEQ ID NO 28
<211> LENGTH: 10
<212> TYPE: PRT
<213> ORGANISM: Homo sapiens

<400> SEQUENCE: 28

Leu Leu Arg Ser Gly Ser Ser Pro Asn Leu
 1               5                  10

<210> SEQ ID NO 29
<211> LENGTH: 10
<212> TYPE: PRT
<213> ORGANISM: Homo sapiens

<400> SEQUENCE: 29

Leu Arg Lys Thr Ala Ser Glu Pro Asn Leu
 1               5                  10

<210> SEQ ID NO 30
<211> LENGTH: 10
<212> TYPE: PRT
<213> ORGANISM: Homo sapiens

<400> SEQUENCE: 30
```

-continued

```
Leu Cys Arg Ser Asn Ser Ile Asp Gly Ser
 1               5                  10

<210> SEQ ID NO 31
<211> LENGTH: 13
<212> TYPE: PRT
<213> ORGANISM: Mus musculus

<400> SEQUENCE: 31

Leu Phe Arg Ser Pro Ser Met Pro Cys Ser Val Ile Arg
 1               5                  10

<210> SEQ ID NO 32
<211> LENGTH: 10
<212> TYPE: PRT
<213> ORGANISM: Rattus norvegicus

<400> SEQUENCE: 32

Leu Arg Leu Ser Ser Ser Ser Gly Arg Leu
 1               5                  10

<210> SEQ ID NO 33
<211> LENGTH: 10
<212> TYPE: PRT
<213> ORGANISM: Mus musculus

<400> SEQUENCE: 33

Ile Glu Arg Thr Leu Ser Val Glu Leu Ser
 1               5                  10

<210> SEQ ID NO 34
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 34

Pro Leu Ser Arg Thr Leu Ser Val Ala Ala Lys
 1               5                  10

<210> SEQ ID NO 35
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

His Leu Met Arg Ser Ala Ser Gly Met His Leu Val Lys Arg Arg
 1               5                  10                  15

<210> SEQ ID NO 36
<211> LENGTH: 10
<212> TYPE: PRT
<213> ORGANISM: Homo sapiens

<400> SEQUENCE: 36

Leu Ser Arg Thr Gln Ser Ser Pro Leu Pro
 1               5                  10

<210> SEQ ID NO 37
<211> LENGTH: 10
```

```
<212> TYPE: PRT
<213> ORGANISM: Homo sapiens

<400> SEQUENCE: 37

Leu Gly Arg Thr Gln Ser Ser Pro Ala Ala
 1               5                  10

<210> SEQ ID NO 38
<211> LENGTH: 10
<212> TYPE: PRT
<213> ORGANISM: Mus musculus

<400> SEQUENCE: 38

Ile Val Arg Thr Asp Ser Val Arg Thr Pro
 1               5                  10

<210> SEQ ID NO 39
<211> LENGTH: 10
<212> TYPE: PRT
<213> ORGANISM: Homo sapiens

<400> SEQUENCE: 39

Leu Leu Arg Ser Gly Thr Ser Pro Asn Leu
 1               5                  10

<210> SEQ ID NO 40
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

His Met Met Arg Ser Ala Ser Gly Met His Leu Val Lys Arg Arg
 1               5                  10                  15

<210> SEQ ID NO 41
<211> LENGTH: 10
<212> TYPE: PRT
<213> ORGANISM: Homo sapiens

<400> SEQUENCE: 41

Leu Leu Arg Ser Gly Ala Ser Pro Asn Leu
 1               5                  10

<210> SEQ ID NO 42
<211> LENGTH: 10
<212> TYPE: PRT
<213> ORGANISM: Homo sapiens

<400> SEQUENCE: 42

Leu Leu Arg Gly Gly Ser Gly Ser Ser Ile
 1               5                  10

<210> SEQ ID NO 43
<211> LENGTH: 10
<212> TYPE: PRT
<213> ORGANISM: Homo sapiens

<400> SEQUENCE: 43

Ile Ala Arg Thr His Thr Asp Val Gly Leu
 1               5                  10

<210> SEQ ID NO 44
```

```
<211> LENGTH: 13
<212> TYPE: PRT
<213> ORGANISM: Rattus norvegicus

<400> SEQUENCE: 44

Ala Arg His Arg Val Thr Lys Thr Gln Val Ala Ile Lys
 1               5                  10

<210> SEQ ID NO 45
<211> LENGTH: 13
<212> TYPE: PRT
<213> ORGANISM: Rattus norvegicus

<400> SEQUENCE: 45

Pro Ala Lys Arg Ile Thr Ile Ala Gln Ile Arg Gln His
 1               5                  10

<210> SEQ ID NO 46
<211> LENGTH: 12
<212> TYPE: PRT
<213> ORGANISM: Rattus norvegicus

<400> SEQUENCE: 46

Ile Asp Arg Gln Arg Thr Val Glu Ser Leu Gln Asn
 1               5                  10

<210> SEQ ID NO 47
<211> LENGTH: 13
<212> TYPE: PRT
<213> ORGANISM: Rattus norvegicus

<400> SEQUENCE: 47

Phe Glu Lys Ile Lys Ser Glu Gly Thr Cys Leu His Arg
 1               5                  10

<210> SEQ ID NO 48
<211> LENGTH: 11
<212> TYPE: PRT
<213> ORGANISM: Rattus norvegicus

<400> SEQUENCE: 48

Leu Lys Ser His Pro Ser Arg Gly Leu Leu His
 1               5                  10

<210> SEQ ID NO 49
<211> LENGTH: 14
<212> TYPE: PRT
<213> ORGANISM: Rattus norvegicus

<400> SEQUENCE: 49

Leu Leu His Gly Asp Thr Met Glu Lys Leu Ile Lys Lys Arg
 1               5                  10

<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 50

His Met Arg Ser Ala Met Ser Gly Leu His Leu Val Lys Arg Arg
 1               5                  10                  15
```

```
<210> SEQ ID NO 51
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 51

His Met Arg Ser Ala Met Ser Gly Met His Leu Val Lys Arg Arg
 1               5                  10                  15

<210> SEQ ID NO 52
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 52

His Leu Met Arg Ser Ala Thr Gly Met His Leu Val Lys Arg Arg
 1               5                  10                  15

<210> SEQ ID NO 53
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)
<223> OTHER INFORMATION: Variable amino acid
<220> FEATURE:
<221> NAME/KEY: MOD_RES
<222> LOCATION: (4)
<223> OTHER INFORMATION: Ser or Thr
<220> FEATURE:
<221> NAME/KEY: MOD_RES
<222> LOCATION: (5)
<223> OTHER INFORMATION: Variable amino acid
<220> FEATURE:
<221> NAME/KEY: MOD_RES
<222> LOCATION: (7)..(9)
<223> OTHER INFORMATION: Variable amino acid

<400> SEQUENCE: 53

Leu Xaa Arg Xaa Xaa Ser Xaa Xaa Xaa Leu
 1               5                  10
```